United States Patent
Quinlan et al.

(10) Patent No.: US 9,700,223 B2
(45) Date of Patent: Jul. 11, 2017

(54) METHOD FOR FORMING A COMPONENT OF A WEARABLE MONITOR

(71) Applicant: LumiraDx UK Ltd, London (GB)

(72) Inventors: Thomas J. Quinlan, Stow, MA (US); Paul J. Gaudet, Dracut, MA (US); David Peabody Goodall, III, Chelmsford, MA (US); John Edgar MacLean, Newton, MA (US)

(73) Assignee: LumiraDx UK Ltd, London (GB)

( * ) Notice: Subject to any disclaimer, the term of this patent is extended or adjusted under 35 U.S.C. 154(b) by 0 days.

(21) Appl. No.: 15/266,767

(22) Filed: Sep. 15, 2016

(65) Prior Publication Data

US 2017/0000372 A1 Jan. 5, 2017

Related U.S. Application Data

(63) Continuation of application No. 14/757,584, filed on Dec. 23, 2015, which is a continuation-in-part of
(Continued)

(51) Int. Cl.
*A61B 5/11* (2006.01)
*A61B 5/0408* (2006.01)
(Continued)

(52) U.S. Cl.
CPC ........ *A61B 5/04085* (2013.01); *A61B 5/0059* (2013.01); *A61B 5/04087* (2013.01);
(Continued)

(58) Field of Classification Search
CPC .............. A61B 5/04; A61B 2560/0214; A61B 2560/0412; A61B 2562/0219;
(Continued)

(56) References Cited

U.S. PATENT DOCUMENTS 3,797,010 A 3/1974 Adler et al.
3,943,918 A 3/1976 Lewis
(Continued)

FOREIGN PATENT DOCUMENTS

EP 0 209 804 A2 1/1987
EP 0 770 349 A1 5/1997
(Continued)

OTHER PUBLICATIONS

Extended European Search Report for European Application No. 14769534.0 dated Oct. 18, 2016.
(Continued)

*Primary Examiner* — Carl Arbes
(74) *Attorney, Agent, or Firm* — Pierce Atwood LLP

(57) ABSTRACT

A health-monitor patch comprising at least one physiological sensor and digital processor is configured to be adhered to the skin of a subject. A health-monitor patch may further include an accelerometer and may detect cardiac waveforms, activity performed by the subject, and a body orientation of the subject. A health-monitor patch may be disposable, in some embodiments, and used for outpatient monitoring. Aspects of noise cancellation and reel-to-reel manufacturing are also described.

12 Claims, 7 Drawing Sheets

Related U.S. Application Data application No. 14/491,441, filed on Sep. 19, 2014, which is a continuation-in-part of application No. 13/840,098, filed on Mar. 15, 2013, which is a continuation-in-part of application No. 13/690,313, filed on Nov. 30, 2012.

(60) Provisional application No. 61/566,528, filed on Dec. 2, 2011.

(51) Int. Cl.
  *A61B 5/00* (2006.01)
  *G01C 22/00* (2006.01)
  *G06F 19/00* (2011.01)

(52) U.S. Cl.
  CPC ........... *A61B 5/1118* (2013.01); *A61B 5/1123* (2013.01); *A61B 5/7203* (2013.01); *A61B 5/7214* (2013.01); *A61B 5/7225* (2013.01); *A61B 5/7271* (2013.01); *A61B 5/742* (2013.01); *G06F 19/3481* (2013.01); *A61B 2560/0214* (2013.01); *A61B 2560/0412* (2013.01); *A61B 2562/0219* (2013.01); *A61B 2562/12* (2013.01); *A61B 2562/125* (2013.01); *A61B 2562/16* (2013.01); *G01C 22/006* (2013.01); *G06F 19/3418* (2013.01)

(58) Field of Classification Search
  CPC .......... A61B 2562/12; A61B 2562/125; A61B 2562/16; A61N 1/04; B23P 17/00; B32B 33/00; G01C 22/006; G01F 19/3418; G01F 19/3481
  See application file for complete search history.

(56) References Cited

U.S. PATENT DOCUMENTS

| | | |
|---|---|---|
| 4,141,367 A | 2/1979 | Ferreira |
| 4,578,769 A | 3/1986 | Frederick |
| 4,791,933 A | 12/1988 | Asai et al. |
| 4,800,894 A | 1/1989 | Milani |
| 4,957,109 A | 9/1990 | Groeger et al. |
| 4,958,645 A | 9/1990 | Cadell et al. |
| 4,974,607 A | 12/1990 | Miwa |
| 5,125,405 A | 6/1992 | Schmid |
| 5,257,631 A | 11/1993 | Wilk |
| 5,294,928 A | 3/1994 | Cooper et al. |
| 5,305,746 A | 4/1994 | Fendrock |
| 5,309,918 A | 5/1994 | Schraag |
| 5,319,363 A | 6/1994 | Welch et al. |
| 5,458,122 A | 10/1995 | Hethuin |
| 5,464,021 A | 11/1995 | Birnbaum |
| 5,515,735 A | 5/1996 | Sarihan |
| 5,538,007 A | 7/1996 | Gorman |
| 5,544,661 A | 8/1996 | Davis et al. |
| 5,579,001 A | 11/1996 | Dempsey et al. |
| 5,579,775 A | 12/1996 | Dempsey et al. |
| 5,600,071 A | 2/1997 | Sooriakumar et al. |
| 5,634,468 A | 6/1997 | Platt et al. |
| 5,682,803 A | 11/1997 | Boianjiu |
| 5,687,734 A | 11/1997 | Dempsey et al. |
| 5,694,940 A | 12/1997 | Unger et al. |
| 5,743,269 A | 4/1998 | Okigami et al. |
| 5,748,103 A | 5/1998 | Flach et al. |
| 5,767,791 A | 6/1998 | Stoop et al. |
| 5,769,755 A | 6/1998 | Henry et al. |
| 5,808,331 A | 9/1998 | Zhang et al. |
| 5,832,490 A | 11/1998 | Riley |
| 5,871,451 A | 2/1999 | Unger et al. |
| 5,882,300 A | 3/1999 | Malinouskas et al. |
| 5,889,211 A | 3/1999 | Maudie et al. |
| 5,899,866 A | 5/1999 | Cyrus et al. |
| 5,910,109 A | 6/1999 | Peters et al. |
| 5,916,159 A | 6/1999 | Kelly et al. |
| 5,917,414 A | 6/1999 | Oppelt et al. |
| 5,919,141 A | 7/1999 | Money et al. |
| 5,938,597 A | 8/1999 | Stratbucker |
| 5,966,692 A | 10/1999 | Langer et al. |
| 5,987,519 A | 11/1999 | Peifer et al. |
| 5,995,861 A | 11/1999 | Price |
| 6,006,125 A | 12/1999 | Kelly et al. |
| 6,013,933 A | 1/2000 | Foerstner et al. |
| 6,018,673 A | 1/2000 | Chin et al. |
| 6,026,321 A | 2/2000 | Miyata et al. |
| 6,057,758 A | 5/2000 | Dempsey et al. |
| 6,066,093 A | 5/2000 | Kelly et al. |
| 6,073,046 A | 6/2000 | Patel et al. |
| 6,076,003 A | 6/2000 | Rogel |
| 6,089,692 A | 7/2000 | Anagnostopoulos |
| 6,150,951 A | 11/2000 | Olejniczak |
| 6,161,036 A | 12/2000 | Matsumura et al. |
| 6,167,290 A | 12/2000 | Yang et al. |
| 6,171,236 B1 | 1/2001 | Bonutti |
| 6,171,237 B1 | 1/2001 | Avitall et al. |
| 6,198,394 B1 | 3/2001 | Jacobsen et al. |
| 6,212,944 B1 | 4/2001 | Kwun et al. |
| 6,331,444 B1 | 12/2001 | Ferrari et al. |
| 6,440,067 B1 | 8/2002 | DeLuca et al. |
| 6,448,621 B1 | 9/2002 | Thakur |
| 6,459,934 B1 | 10/2002 | Kadhiresan |
| 6,529,771 B1 | 3/2003 | Kieval et al. |
| 6,539,613 B1 | 4/2003 | Ulmer |
| 6,544,171 B2 | 4/2003 | Beetz et al. |
| 6,544,173 B2 | 4/2003 | West et al. |
| 6,544,174 B2 | 4/2003 | West et al. |
| 6,579,231 B1 | 6/2003 | Phipps |
| 6,586,810 B2 | 7/2003 | Thakur |
| 6,623,312 B2 | 9/2003 | Merry et al. |
| 6,794,900 B2 | 9/2004 | Tang et al. |
| 6,847,892 B2 | 1/2005 | Zhou et al. |
| 6,870,484 B1 | 3/2005 | Brinsfield et al. |
| 6,904,313 B1 | 6/2005 | Snell |
| 6,911,727 B1 | 6/2005 | Martin et al. |
| 6,997,882 B1 | 2/2006 | Parker et al. |
| 7,280,040 B2 | 10/2007 | Devaul |
| 7,318,417 B2 | 1/2008 | Lang et al. |
| 7,382,247 B2 | 6/2008 | Welch et al. |
| 7,439,856 B2 | 10/2008 | Weiner et al. |
| 7,486,980 B2 | 2/2009 | Lin et al. |
| 7,508,064 B2 | 3/2009 | Martin et al. |
| 7,515,043 B2 | 4/2009 | Welch et al. |
| 7,515,044 B2 | 4/2009 | Welch et al. |
| 7,563,632 B2 | 7/2009 | Martin et al. |
| 7,647,196 B2 | 1/2010 | Kahn et al. |
| 7,653,508 B1 | 1/2010 | Kahn et al. |
| 7,753,861 B1 | 7/2010 | Kahn et al. |
| 7,881,902 B1 | 2/2011 | Kahn et al. |
| 7,981,058 B2 | 7/2011 | Akay |
| 7,987,070 B2 | 7/2011 | Kahn et al. |
| 8,180,591 B2 | 5/2012 | Yuen et al. |
| 8,214,007 B2 | 7/2012 | Baker et al. |
| 8,630,699 B2 | 1/2014 | Baker et al. |
| 8,750,974 B2 | 6/2014 | Baker et al. |
| 8,965,492 B2 | 2/2015 | Baker et al. |
| 9,155,484 B2 | 10/2015 | Baker et al. |
| 9,237,848 B2 | 1/2016 | Russell |
| 2001/0023315 A1 | 9/2001 | Flach et al. |
| 2002/0055671 A1 | 5/2002 | Wu et al. |
| 2002/0091785 A1 | 7/2002 | Ohlenbusch et al. |
| 2002/0106709 A1 | 8/2002 | Potts et al. |
| 2002/0122519 A1 | 9/2002 | Douglas et al. |
| 2003/0001742 A1 | 1/2003 | Eshelman et al. |
| 2003/0004549 A1 | 1/2003 | Hill et al. |
| 2003/0055460 A1 | 3/2003 | Owen et al. |
| 2003/0149349 A1 | 8/2003 | Jensen |
| 2003/0208113 A1 | 11/2003 | Mault et al. |
| 2003/0208335 A1 | 11/2003 | Unuma et al. |
| 2003/0236452 A1 | 12/2003 | Melker et al. |
| 2004/0030258 A1 | 2/2004 | Williams et al. |
| 2004/0034293 A1 | 2/2004 | Kimball |
| 2004/0113806 A1 | 6/2004 | Neykov |
| 2004/0242976 A1 | 12/2004 | Abreu |

(56) References Cited

U.S. PATENT DOCUMENTS

| | | |
|---|---|---|
| 2004/0252031 A1 | 12/2004 | Taylor |
| 2005/0116820 A1 | 6/2005 | Goldreich |
| 2005/0137489 A1 | 6/2005 | Jackson et al. |
| 2005/0206518 A1 | 9/2005 | Welch et al. |
| 2005/0216334 A1 | 9/2005 | Mehrabani-Farsi |
| 2005/0234314 A1 | 10/2005 | Suzuki et al. |
| 2005/0245839 A1 | 11/2005 | Stivoric et al. |
| 2006/0044856 A1 | 3/2006 | Bird et al. |
| 2006/0063980 A1 | 3/2006 | Hwang et al. |
| 2006/0074284 A1 | 4/2006 | Juola et al. |
| 2006/0136001 A1 | 6/2006 | Ortega et al. |
| 2006/0183434 A1 | 8/2006 | Westra et al. |
| 2006/0189976 A1 | 8/2006 | Karni et al. |
| 2006/0205171 A1 | 9/2006 | Tsukada |
| 2006/0238333 A1 | 10/2006 | Welch et al. |
| 2007/0013511 A1 | 1/2007 | Weiner et al. |
| 2007/0069887 A1 | 3/2007 | Welch et al. |
| 2007/0073132 A1 | 3/2007 | Vosch |
| 2007/0073178 A1 | 3/2007 | Browning et al. |
| 2007/0073514 A1 | 3/2007 | Nogimori et al. |
| 2007/0191728 A1 | 8/2007 | Shennib |
| 2007/0197920 A1 | 8/2007 | Adams |
| 2007/0270678 A1 | 11/2007 | Fadem et al. |
| 2007/0285226 A1 | 12/2007 | Yi |
| 2007/0293781 A1 | 12/2007 | Sims et al. |
| 2008/0079589 A1 | 4/2008 | Blackadar |
| 2008/0139953 A1 | 6/2008 | Baker et al. |
| 2008/0140338 A1 | 6/2008 | No et al. |
| 2008/0275317 A1 | 11/2008 | Cho et al. |
| 2008/0275327 A1* | 11/2008 | Faarbaek ............ A61B 5/0002 600/382 |
| 2009/0018409 A1 | 1/2009 | Banet et al. |
| 2009/0043185 A1 | 2/2009 | McAdams et al. |
| 2009/0047645 A1 | 2/2009 | DiBenedetto et al. |
| 2009/0131759 A1 | 5/2009 | Sims et al. |
| 2009/0132197 A1 | 5/2009 | Rubin et al. |
| 2009/0192391 A1 | 7/2009 | Lovitt et al. |
| 2009/0259265 A1* | 10/2009 | Stevenson ............ A61N 1/0556 607/2 |
| 2009/0264337 A1 | 10/2009 | Angelides |
| 2009/0319221 A1 | 12/2009 | Kahn et al. |
| 2010/0145202 A1 | 6/2010 | Mclaughlin et al. |
| 2010/0160762 A1 | 6/2010 | McLaughlin et al. |
| 2010/0217533 A1 | 8/2010 | Nadkarni et al. |
| 2010/0256947 A1 | 10/2010 | Kim et al. |
| 2010/0298653 A1 | 11/2010 | McCombie et al. |
| 2010/0298661 A1 | 11/2010 | McCombie et al. |
| 2010/0324390 A1 | 12/2010 | McLaughlin et al. |
| 2011/0054290 A1 | 3/2011 | Derchak |
| 2011/0054359 A1 | 3/2011 | Sazonov et al. |
| 2011/0066053 A1 | 3/2011 | Yazicioglu |
| 2011/0066064 A1 | 3/2011 | Jangle et al. |
| 2011/0066383 A1 | 3/2011 | Jangle et al. |
| 2011/0191158 A1 | 8/2011 | Kateraas et al. |
| 2011/0288379 A1 | 11/2011 | Wu |
| 2012/0071770 A1 | 3/2012 | Grey et al. |
| 2012/0083714 A1 | 4/2012 | Yuen et al. |
| 2012/0108920 A1 | 5/2012 | Bly et al. |
| 2012/0226117 A1 | 9/2012 | Lamego et al. |
| 2012/0245439 A1 | 9/2012 | Andre et al. |
| 2013/0006125 A1 | 1/2013 | Kroll et al. |
| 2013/0009993 A1 | 1/2013 | Horseman |
| 2013/0060115 A1 | 3/2013 | Gehman et al. |
| 2013/0096843 A1 | 4/2013 | Yuen et al. |
| 2013/0116533 A1 | 5/2013 | Lian et al. |
| 2013/0158686 A1 | 6/2013 | Zhang et al. |
| 2013/0190903 A1 | 7/2013 | Balakrishnan et al. |
| 2013/0217979 A1 | 8/2013 | Blackadar et al. |
| 2013/0261422 A1 | 10/2013 | Gilmore et al. |
| 2014/0100432 A1 | 4/2014 | Golda et al. |
| 2014/0156043 A1 | 6/2014 | Blackadar et al. |
| 2014/0206976 A1 | 7/2014 | Thompson et al. |
| 2014/0275932 A1 | 9/2014 | Zadig |
| 2015/0073231 A1 | 3/2015 | Beck et al. |
| 2015/0119728 A1 | 4/2015 | Blackadar et al. |
| 2015/0148637 A1 | 5/2015 | Golda et al. |
| 2015/0265173 A1 | 9/2015 | Datovech et al. |
| 2016/0029917 A1 | 2/2016 | Baker et al. |
| 2016/0029918 A1 | 2/2016 | Baker et al. |
| 2016/0128598 A1 | 5/2016 | Takizawa et al. |
| 2016/0242654 A1 | 8/2016 | Quinlan et al. |
| 2017/0000371 A1 | 1/2017 | Quinlan et al. |

FOREIGN PATENT DOCUMENTS

| | | |
|---|---|---|
| EP | 0 665 584 B1 * | 4/1999 |
| EP | 0 910 985 A1 | 4/1999 |
| EP | 14769534.0 | 10/2016 |
| EP | PCT/EP2016/069546 | 10/2016 |
| JP | 11-088546 A2 | 3/1990 |
| JP | 11-042214 A2 | 2/1999 |
| WO | WO 96/20641 A1 | 7/1996 |
| WO | WO 96/29005 A1 | 9/1996 |
| WO | WO 97/46156 A1 | 12/1997 |
| WO | WO 99/59460 A2 | 11/1999 |
| WO | WO 01/89362 A2 | 11/2001 |
| WO | WO 01/97686 A1 | 12/2001 |
| WO | WO 01/89362 A3 | 2/2004 |
| WO | WO 2008/057884 A2 | 5/2008 |
| WO | WO 2008/142365 A1 | 11/2008 |
| WO | WO 2009/056859 A1 | 5/2009 |
| WO | WO 2009/083032 A1 | 7/2009 |
| WO | WO 2012/127370 A1 | 9/2012 |
| WO | WO 2012/140322 A1 | 10/2012 |

OTHER PUBLICATIONS

International Search Report and Written Opinion for International Application No. PCT/EP2016/069546 dated Oct. 31, 2016.

Friel, Efficiency Factor and Decoupling. TrainingPeaks. http://home.trainingpeaks.com/blog/article/efficiency-factor-and-decoupling Dec. 7, 2011[last accessed Oct. 25, 2016].

[No Author Listed] U.S. Department of Health and Human Services (2006). General Physical Activities Defined by Level of Intensity. Physical activity for everyone: measuring physical activity intensity: metabolic equivalent (MET) level. Retrieved from http://www.cdc.gov/nccdphp/dnpa/physical/pdf/PA_Intensity_table_2_1.pdf; pp. 1-5.

Casale et al., Personalization and user verification in wearable systems using biometric walking patterns. Pers Ubiquit Comput. Jul. 2011:18pgs.

Invitation to Pay Additional Fees for Application No. PCT/US2012/067310 mailed Mar. 13, 2013.

International Search Report and Written Opinion for PCT/US2012/067310 mailed May 13, 2013.

International Preliminary Report on Patentability for PCT/US2012/067310 mailed Jun. 12, 2014.

International Search Report and Written Opinion for PCT/US2014/022624 mailed Jul. 9, 2014.

International Preliminary Report on Patentability for PCT/US2014/022624 mailed Sep. 24, 2015.

International Search Report and Written Opinion for PCT/US2014/056532 mailed Dec. 29, 2014.

International Preliminary Report on Patentability for PCT/US2014/056532 mailed Sep. 1, 2016.

Bassett et al., Accelerometer-Based Physical Activity: Total Volume per Day and Standardized Measures. Med Sci Sports Exerc. Aug. 6, 2014 [Epub ahead of print]. 24 pages.

Boyd et al., A Framework to Detect and Classify Activity Transitions in Low-Power Applications. ICME'09: Proceedings of the 2009 IEEE International Conference on Multimedia and Expo. Jun. 2009.

Fimbel et al., Event identification in movement recordings by means of qualitative patterns. Neuroinformatics. 2003;1(3):239-57.

Han Alainen et al., Jerk-based feature extraction for robust activity recognition from acceleration data. 11th Intl. Conf. on Intelligent Sys. Design and App. 2011:831-6.

Helmi et al., Human activity recognition using a fuzzy inference system. Fuzzy Systensm 2009. Fuzz-IEEE 2009. IEEE International Conference.

(56) References Cited

OTHER PUBLICATIONS

Kawahara et al., Monitoring daily energy expenditure using a 3-axis accelerometer with a low-power microprocessor. Int J Hum-Comput Interact. Mar. 2009;1(5):145-154.

Khan, Accelerometer's Position Free Human Activity Recognition Using a Hierarchical Recognition Model. E-Health Networking Applications and Services (Healthcom). 2010 12th IEEE International Conference. Jul. 1-3, 2010. pp. 296-301.

Lee et al., Physical activity recognition using a single tri-axis accelerometer. Proceedings of the World Congress on Engineering and Computer Science (WCECS). 2009. San Francisco, USA. 1:14-17.

Mohammad et al., Human activity recognition using a fuzzy inference system. Fuzzy Systems, 2009. FUZZ-IEEE 2009. IEEE International conference on IEEE, 2009.

Weyand et al., Ambulatory estimates of maximal aerobic power from foot-ground contact times and heart rates in running humans. J Appl Physiol (1985). Jul. 2001;91(1):451-8.

* cited by examiner

METHOD FOR FORMING A COMPONENT OF A WEARABLE MONITOR

RELATED APPLICATIONS

This is a continuation of U.S. application Ser. No. 14/757,584, entitled "A HEALTH-MONITOR PATCH," filed on Dec. 23, 2015, which is a continuation-in-part of U.S. application Ser. No. 14/491,441, entitled "HEALTH MONITOR," filed on Sep. 19, 2014, which is a continuation-in-part of U.S. application Ser. No. 13/840,098, entitled "VERSATILE SENSORS WITH DATA FUSION FUNCTIONALITY," filed on Mar. 15, 2013, which is a continuation-in-part of U.S. application Ser. No. 13/690,313, entitled "INTELLIGENT ACTIVITY MONITORING," filed on Nov. 30, 2012, which claims the benefit under 35 U.S.C. §119(e) to U.S. Provisional application Ser. No. 61/566,528, entitled "INTELLIGENT ACTIVITY MONITORING," filed on Dec. 2, 2011. The entire contents of each of the foregoing applications is incorporated herein by reference.

FIELD

The technology relates to wearable devices that are configured to monitor physiological parameters (heart rate, heart rate variability, respiratory rate, etc.) of a subject and/or physical activity performed by the subject.

BACKGROUND

There currently exist small sensing devices that can be worn by a user to monitor physical activity performed by the user. As an example, the FitLinxx® ActiPed+ (available from FitLinxx, Shelton, Conn., USA) is a small device that can be clipped to a shoe and used to monitor walking and running activities by the user. When a user walks or runs, an on-board accelerometer outputs data that is stored on the device for subsequent transmission to a computer system. The computer system can analyze the data to determine activity type, and calculate various activity parameters (e.g., duration of activity, total steps, distance traveled, and calories burned). Results of the data analysis may be presented on the computer's display, so that a user may review details of his or her activity. The results may be stored, so that the user can maintain a record of exercise regimens and track progress toward exercise goals, or so that the data may be used by medical personnel to track recovery from an illness or injury. Other modern activity monitors perform similar functions with varying degrees of accuracy.

Most activity monitors are configured to be attached to a subject's clothing or strapped to a subject's limb. For example, some activity monitors may clip on clothing, or be configured to clip on or lace in a shoe. Activity monitors that attach to clothing are generally not adapted to sense a physiological parameter of the subject. Some activity monitors that may be worn on the wrist or ankle of a subject may be adapted to sense heart rate, but these monitors generally cannot measure details of cardiac waveform to obtain information such as heart-rate variability (HRV) or cardiac abnormalities such as arrhythmias.

SUMMARY OF EXAMPLE EMBODIMENTS

An adhesive, health-monitor patch that can be adhered to the skin of a subject in the vicinity of the heart is described. In some embodiments, the health-monitor patch comprises a flexible and waterproof strip, and is designed to be worn for extended periods of time. Two monitoring electrodes on the strip may contact the skin of the subject and be used to collect cardiac waveform data. At least a third electrode may be included to suppress electrical noise and improve the quality of data collected by the health-monitor patch. The cardiac waveform data may be analyzed to determine various physiological parameters of a subject, such as heart rate, heart-rate variability, caloric burn, resting heart rate, recovery from a workout, respiratory rate, etc. The health-monitor patch may further include an accelerometer from which acceleration data may be analyzed to determine parameters associated with motion of the subject (e.g., body orientation of the subject, type of activity performed by the subject, intensity of activity performed by the subject, etc.).

Some embodiments of a health-monitor patch may comprise a flexible strip assembly, which may house electrical components of the health-monitor patch, and a replaceable electrode strip that adheres to the flexible strip assembly. The replaceable electrode strip may provide replaceable adhesion and electrical connections between the subject and the flexible strip assembly. Other embodiments of the health-monitor patch may be single-use, disposable strips that include electronics and adhesive layers for attaching to a subject's skin. A disposable health-monitor patch may be a low-cost device suitable for single-use applications, such as for out-patient health monitoring.

A health-monitor patch may include an accelerometer, processor, and machine-readable instructions that adapt the health-monitor patch to perform a variety of different functions and data analyses as described, for example, in U.S. Patent Application Pub. No. 2015-0119728 and in U.S. Patent Application Pub. No. 2013-0217979, the disclosures of which were incorporated by reference above in their entirety.

According to some embodiments, a health-monitor patch may comprise a cardiac sensor comprising two monitor electrodes that are configured to receive two signals from two locations on the skin of the subject. A health-monitor patch may further include a noise electrode configured to receive a signal from the skin of the subject at a location separate from the two locations of the two monitor electrodes. A health-monitor patch may further include an electronic assembly comprising a processor configured to process signals from the two monitor electrodes.

Some embodiments relate to methods for operating a health-monitor patch. Some methods of operation may include acts of receiving two electrical signals at two monitor electrodes of the health-monitor patch, wherein the two monitor electrodes contact the skin of a subject and are separated by a distance, conducting electrical signals from the two monitor electrodes over two conductive paths to two signal inputs of an electronic circuit mounted within the health-monitor patch, receiving an electrical signal from a noise electrode that contacts the skin of the subject and is located between the two monitor electrodes, and conducting the electrical signal from the noise electrode to a conductive shield, such as an ESD shield, that extends at least part way over the two conductive paths. The conductive shield may also extend over the electronic circuit.

The foregoing and other aspects, embodiments, and features of the present teachings can be more fully understood from the following description in conjunction with the accompanying drawings.

BRIEF DESCRIPTION OF THE DRAWINGS

The skilled artisan will understand that the figures, described herein, are for illustration purposes only. It is to be understood that in some instances various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

The features and advantages of the present invention will become more apparent from the detailed description set forth below when taken in conjunction with the drawings.

DETAILED DESCRIPTION OF EXAMPLE EMBODIMENTS

Figure 1A:
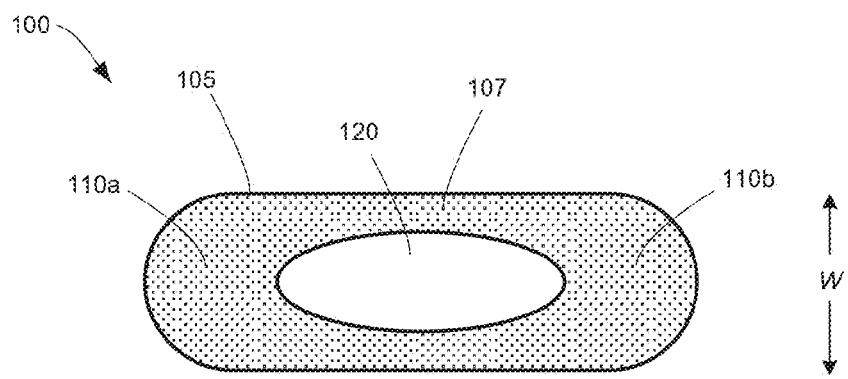
FIG. 1A depicts a plan view of a health-monitor patch, according to some embodiments.

An example embodiment of a health-monitor patch 100 is depicted in FIG. 1A. According to some embodiments, a health-monitor patch may be formed from flexible materials and configured to adhere to the skin of a person. A health-monitor patch may include at least one accelerometer for sensing motion and/or activities of a subject, and/or may include electrodes, one or more lasers, one or more light-emitting diodes, one or more photodiodes, one or more temperature sensors and/or other sensors for sensing one or more physiological parameters of a subject. The inventors have recognized and appreciated that a flexible patch-type device that having electrodes and/or other sensors that can directly contact a subject's skin can provide more accurate information about a subject's biophysical parameters (such as cardiac waveform, body temperature, respiratory rate, blood oxygenation level, blood glucose level, etc.), which conventional pedometers may not be able to provide. To obtain a reliable cardiac waveform signal, such a patch device is preferably located in the vicinity of a subject's heart and includes two or more electrodes spaced a distance apart. Accordingly, a health-monitor patch is preferably flexible so that it's sensing electrodes can remain in contact with the skin of the subject as the subject moves.

The inventors have also recognized and appreciated that a health-monitor patch attached to a subject's torso can provide more reliable information about a subject's position (lying, sitting, standing) than a conventional activity monitor that straps to a subject's wrist or ankle. Torso orientation can be helpful when identifying a type of activity that a subject is performing (e.g., distinguishing rowing from cycling or cycling from running) or identifying a resting state of a subject. Torso orientation can also be helpful when monitoring patients. For example, an increased heart rate accompanied by data indicating the patient has changed from a lying position to a vertical and/or walking orientation may be of no concern, whereas an increased heart rate while the patient remains in a lying position may require the attention of a caregiver.

The inventors have further conceived of structures, circuits, processes, and combinations of materials that provide a waterproof health-monitor patch, according to some embodiments, and a low-cost disposable health-monitor patch, according to some embodiments. Further details of a health-monitor patch are described below.

Referring again to FIG. 1A, a health-monitor patch 100 may include a first end region 110a and a second end region 110b. A health-monitor patch may comprise a flexible strip assembly 105 that may or may not have an open center 120. For embodiments that include an open center, one or more flexible ribs 107 may connect the first end region 110a and the second end region 110b. For embodiments that do not have an open center 120, a center portion of the flexible strip assembly 105 may be thin or otherwise configured to provide flexible bending and twisting between the first end region and the second end region. A width W of a health-monitor patch 100 may be between approximately 10 mm and approximately 50 mm, according to some embodiments.

Figure 1B:
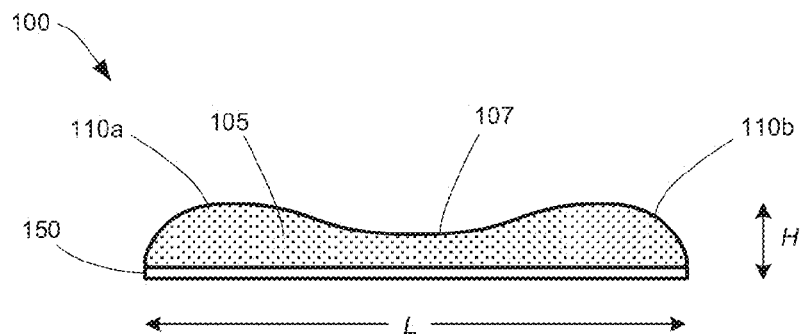
FIG. 1B depicts an elevation view of a health-monitor patch, according to some embodiments.

An elevation view of a health-monitor patch 100 is depicted in FIG. 1B. In some embodiments, a health-monitor patch may comprise enlarged lobes at the end regions 110a, 110b as shown in the drawing. Electronics of a health-monitor patch may be housed within the lobes. An overall length L of a health-monitor patch 100 may be between approximately 50 mm and approximately 150 mm. A height H of a health-monitor patch may be between approximately 3 mm and approximately 10 mm. The flexible strip assembly may comprise a flexible polymer such as, but not limited to, silicone.

According to some embodiments, a replaceable electrode strip 150 may be adhered, temporarily, to a lower surface of a health-monitor patch 100, as depicted in FIG. 1B. The replaceable electrode strip may provide adhesion, electrical connections, and a waterproof seal between the flexible strip assembly and the skin of a subject. The replaceable electrode strip may be peeled off of the lower surface of the flexible strip assembly 105 and replaced with a new replaceable electrode strip 150. For example, a user may adhere a health-monitor patch 100 to their skin for a period of time (e.g., one or several days, a week, or more), and then remove the health-monitor patch, replace the replaceable electrode strip 150, and then re-adhere the health-monitor patch to their skin for continued monitoring of activity and physiological parameters.

Figure 1C:
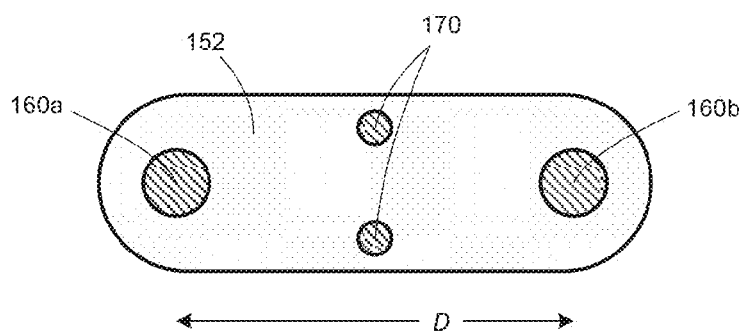
FIG. 1C depicts an underside view of a health-monitor patch, according to some embodiments.

A bottom-side or skin-side view of a health-monitor patch having a replaceable electrode strip 150 is illustrated in FIG. 1C, according to some embodiments. The replaceable electrode strip may include an adhesion surface 152 configured to adhere to a subject's skin. The replaceable electrode strip may comprise two or more electrodes 160a, 160b that provide electrical contact to the subject's skin, and electrically connect with electronic circuitry inside the flexible strip assembly 105. In some embodiments, a first monitor electrode 160a is located at a first end of the replaceable electrode strip 150, and a second monitor electrode 160b is located at a second end of the replaceable electrode strip. A distance D between the first monitor electrode and second monitor electrode may be between approximately 50 mm and approximately 90 mm. The first monitor electrode 160a and second monitor electrode 160b may comprise hydrogel electrodes in some embodiments, or may comprise other flexible electrodes for contacting a subject's skin. A width of the replaceable electrode strip 150 may be between approximately 10 mm and approximately 50 mm, according to some embodiments.

In some cases, there may be one or more noise electrodes 170 located separately from the first monitor electrode 160a and the second monitor electrode 160b. As shown, in some embodiments, the noise electrode(s) 170 may be located between the monitor electrodes 160a, 160b. A noise electrode may also comprise a hydrogel electrode or other flexible electrode. For some implementations, a noise electrode 170 may be located approximately half-way between the first monitor electrode and the second monitor electrode. In other embodiments, one or more noise electrodes may be placed closer to one or the other of the first monitor electrode and second monitor electrode or at other locations on the strip 150. A noise electrode may provide an electrical contact to the skin of a subject and further connect electrically to noise cancellation circuitry within the flexible strip assembly 105.

Figure 2A:
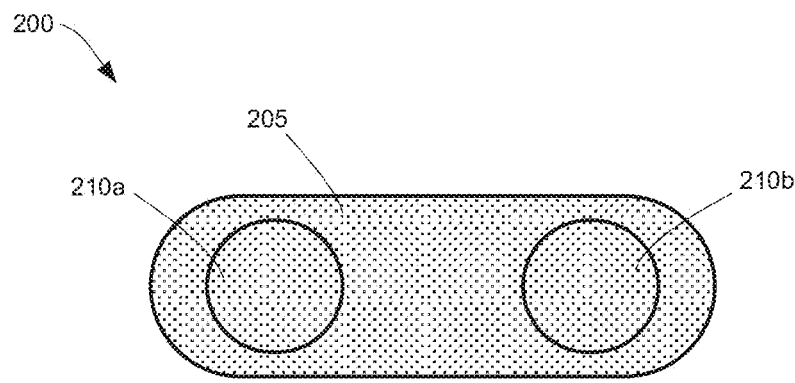
FIG. 2A depicts a plan view of a disposable health-monitor patch, according to some embodiments.
Figure 2B:
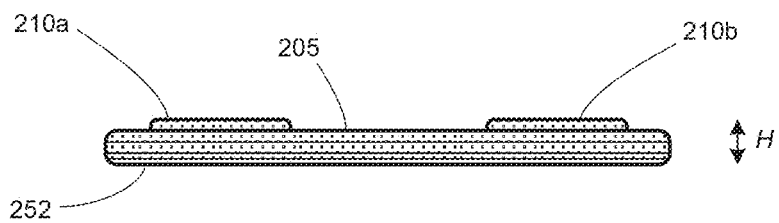
FIG. 2B depicts an elevation view of a disposable health-monitor patch, according to some embodiments.

A second embodiment of a health-monitor patch is depicted in FIG. 2A. As shown, in some embodiments, a disposable health-monitor patch 200 may comprise a flexible strip assembly 205 that includes a first end region 210a and a second and region 210b. The length L and width W of a disposable health-monitor patch 200 may be of approximately the same corresponding dimensions for a health-monitor patch 100 described above in connection with FIG. 1A. Referring to FIG. 2B, a disposable health-monitor patch 200 may have a lower profile, and a height that is between approximately 2 mm and approximately 8 mm. A flexible strip assembly 205 may be more uniform in height along its length, and formed from a plurality of flexible layers of materials. In some embodiments, it may include bulged end regions 210a, 210b that accommodate the device's electronics (e.g., a PCB assembly and battery).

A disposable health-monitor patch 200 may not have a replaceable electrode strip 150, but may include an adhesion surface 252. A disposable health-monitor patch 200 may have a release liner (shown in FIG. 7A) located over the adhesion surface 252 that may be removed just prior to adhesion of the disposable health-monitor patch to the skin of a subject. A disposable health-monitor patch may operate between approximately one day and approximately 14 days on a subject, and then be removed and disposed.

Figure 2C:
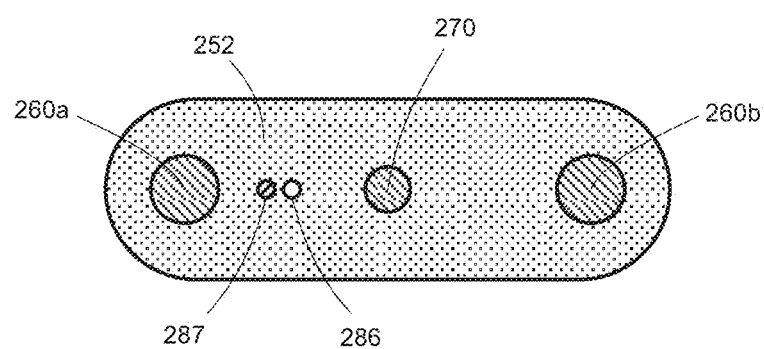
FIG. 2C depicts an underside view of a disposable health-monitor patch, according to some embodiments.

A plan-view illustration of an adhesion surface 252 of a disposable health-monitor patch 200 is depicted in FIG. 2C, according to some embodiments. The adhesion surface 252 may accommodate a first monitor electrode 260a and a second monitor electrode 260b. The monitor electrodes may be separated by a distance between approximately 50 mm and approximately 90 mm, according to some implementations. Between the monitor electrodes, or at some other location on the adhesion surface 252, there may be one or more noise electrodes 270. The monitor electrodes may provide an electrical connection to the patient's skin and to sensing and data analysis circuitry within the disposable health-monitor patch. The one or more noise electrodes may provide electrical connection to the subject's skin and to noise cancellation circuitry within the disposable health-monitor patch 200. In some embodiments, there may be one or more openings through the adhesion surface 252 for radiation to pass through from one or more light-emitting devices 286 (e.g., laser(s), LED(s)), and for backscattered light to pass through to one or more photodiodes 287.

In operation, a health-monitor patch may collect physiological data (e.g., cardiac data, temperature data, blood oxygenation data, etc.) and/or motion data (e.g., accelerometer data) from one or more of its sensors. In some embodiments, some of the data may be processed or pre-processed by an on-board processor of the health-monitor patch. In some implementations, collected data may be offloaded to a remote device (e.g., a smart phone, a laptop, a tablet, a computer, etc.) which may process the collected data. Data accumulated on a health-monitor patch may be downloaded via a wireless connection. Examples of data processing and data transfer are described in further detail in U.S. Patent Application Pub. No. 2015-0119728, incorporated by reference above.

Figure 3:
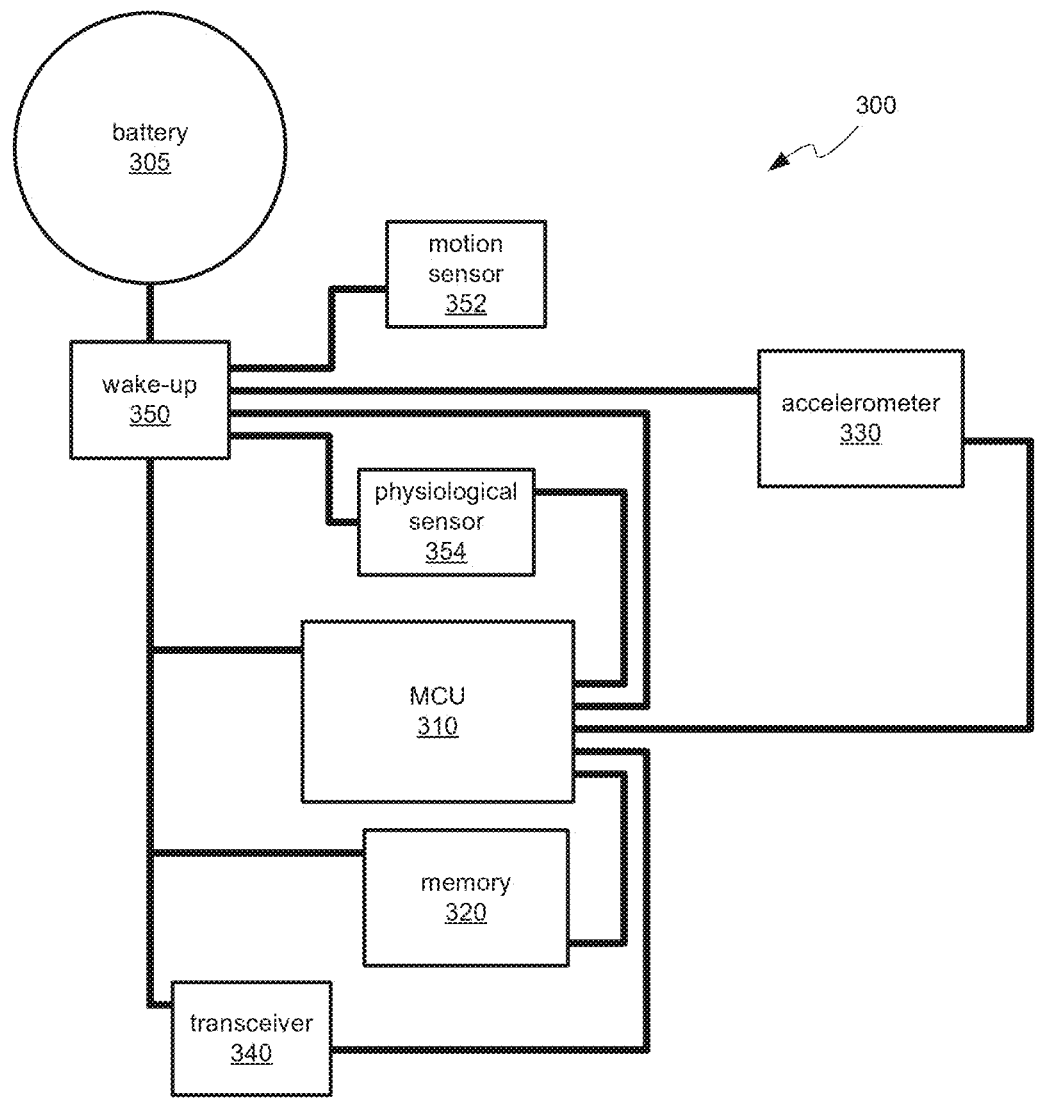
FIG. 3 illustrates electronic components that may be included in a health-monitor patch, according to some embodiments.

FIG. 3 depicts some components and an example circuit 300 that may be implemented in a health-monitor patch, according to some embodiments. As shown, a health-monitor patch's circuitry may, for example, comprise a source of power 305 (e.g., at least one battery or energy-scavenging chip and a wake-up and power-management circuit 350) that provide and manage power delivery to one or more of an accelerometer 330, a digital processor 310, memory 320, and a transceiver 340. The processor 310 may be coupled to one or more of the wake-up circuit, the accelerometer, memory, and the transceiver. The power source 305 and/or processor 310 may be coupled to additional components, such as one or more physiological sensors 354.

The term "digital processor" or "processor" as used herein may refer to at least one microcontroller, microprocessor, digital signal processor (DSP), application-specific integrated circuit (ASIC), field-programmable gate array (FPGA), or data-processing logic circuitry. "Digital processor" or "processor" may also be used to refer to any combination of the foregoing digital processing devices, including more than one of a particular data processing device.

The processor may be configured to receive and process data from one or more sensors on the health-monitor patch (e.g., from the accelerometer 330 and/or one or more physiological sensors 354). The processor 310 may further be configured to read and write data to memory 320, and to send and receive data from transceiver 340. The wake-up circuit 350 may be adapted to sense when the health-monitor patch is not in use, and in response, reduce power consumption of the internal circuit 300, according to some embodiments. The wake-up circuit may be further adapted to sense when the health-monitor patch is placed in use, and in response, activate one or more elements of the internal circuit 300.

In some embodiments, the processor 310 may, for example, comprise a low-power, 8-bit processor configured to draw low power in sleep-mode operation, and capable of operating at multiple millions of instructions per second (MIPS) when activated. One example of a suitable processor is the 8051F931 processor available from Silicon Laboratories Inc. of Austin, Tex. Another example of a processor is the nRF51822 processor available from Nordic Semiconductor of Oslo, Norway, though any other suitable processor or microprocessor may alternatively be employed in other embodiments. In some implementations, the processor 310 may support radio-frequency communications with other devices. A balun (e.g., BAL-NRF 02D3 available from ST Microelectronics of Geneva, Switzerland) may be used to match RF signals between an antenna and the processor, according to some embodiments.

The processor 310 may, for example, include various types of on-board memory (e.g., flash memory, SRAM, and XRAM) for storing data and/or machine-readable instructions, and may be clocked by an internal oscillator or external oscillator. In some embodiments, the processor may, for example, be clocked by an internal high-frequency oscillator (e.g., an oscillator operating at about 25 MHz or higher) when the processor is active and processing data, and alternatively clocked by a low-frequency oscillator (external or internal to the processor) when the processor is substantially inactive and in sleep mode. The clocking of the processor at low frequency may, for example, reduce power consumption by the processor during sleep mode. The low-frequency clocking may be at a frequency that is less than 50% of the high-frequency clocking in some embodiments, less than 20% of the high-frequency clocking in some embodiments, less than 10% of the high-frequency clocking in some embodiments, less than 5% of the high-frequency clocking in some embodiments, less than 2% of the high-frequency clocking in some embodiments, less than 1% of the high-frequency clocking in some embodiments, and yet less than 0.1% in some embodiments.

In various embodiments, the processor 310 may be configured to receive acceleration data from accelerometer 330 and process the received data according to pre-programmed machine-readable instructions that are loaded onto and execute on the processor. The processor 310 may, for example, be configured to receive analog and/or digital input data, and may include on-board analog-to-digital and digital-to-analog converters and on-board timers or clocks. According to some embodiments, the processor may also be configured to receive and analyze cardiac waveform data from electrodes in contact with a user's skin. In some embodiments, the processor may be further configured to receive power through wake-up and power management circuitry 350. The processor may, in some embodiments, cooperate with or comprise a portion or all of power management circuitry 350, and facilitate activating and deactivating one or more circuit elements within the health-monitor patch.

In some embodiments, the processor 310 may be configured to operate at a number of different clock frequencies. When operating at a low clock frequency, the processor will typically consume less power than when operating at a high clock frequency. In some embodiments, the processor may, for example, be configured to be in a "sleep" mode and operating at a low clock frequency when there is no motion of health-monitor patch, and to be cycled through several operating states when motion of the health-monitor patch is detected. As one example, when in sleep mode, the processor may sample data at a rate less than 10 Hz and draw less than about 30 microamps.

In some embodiments, accelerometer 330 may, for example, comprise a multi-axis accelerometer and/or gyroscopes configured to sense acceleration along at least two substantially orthogonal spatial directions. The accelerometer 330 may, for example, comprise a three-axis accelerometer based on micro-electro-mechanical systems (MEMS) technology. In some implementations, one or more single-axis accelerometers may additionally or alternatively be used. In some embodiments, the accelerometer 330 may be configured to provide one or more analog data-stream outputs (e.g., X, Y, Z data outputs corresponding to each axis of the accelerometer) that are each representative of a magnitude and direction of acceleration along a respective axis. One example of a suitable accelerometer is the Kionix model KXSC7 accelerometer available from Kionix Inc., Ithaca, N.Y. Another example of a suitable accelerometer is the LIS2DH accelerometer available from ST Microelectronics of Geneva, Switzerland. The accelerometer 330 may, for example, provide analog output data, that may later be converted to digital data, or may provide digital output data representative of acceleration values.

The accelerometer 330 may be characterized by several parameters. Among these parameters may, for example, be a sensitivity value and a sampling rate value. As examples, the accelerometer's analog sensitivity may be between about 100 millivolts (mV) per gravitational value (100 mV/G) and about 200 mV/G in some embodiments, between about 200 mV/G and about 400 mV/G in some embodiments, between about 400 mV/G and about 800 mV/G in some embodiments, and yet between about 800 mV/G and about 1600 mV/G in some embodiments. When configured to provide a digital output, the sampling rate of the accelerometer may, for example, be between about 10 samples per second per axis (10 S/sec-A) and about 20 S/sec-A in some embodiments, between about 20 S/sec-A and about 40 S/sec-A in some embodiments, between about 40 S/sec-A and about 80 S/sec-A in some embodiments, between about 80 S/sec-A and about 160 S/sec-A in some embodiments, between about 160 S/sec-A and about 320 S/sec-A in some embodiments, and yet between about 320 S/sec-A and about 640 S/sec-A in some embodiments. It will be appreciated that in some embodiments the higher sampling rates may improve the quality of the measured accelerations.

It will be appreciated that, in some embodiments, an accelerometer 330 may be combined with one or more analog-to-digital converters to provide digital output data representative of acceleration values at sampling rates described above. When digital output data is provided by an accelerometer, the accelerometer's sensitivity may be expressed in units of bits per gravitational constant (b/G). As examples, an accelerometer providing digital output data may have a sensitivity of more than about 2 b/G in some embodiments, more than about 4 b/G in some embodiments, more than about 6 b/G in some embodiments, more than about 8 b/G in some embodiments, more than about 10 b/G in some embodiments, more than about 12 b/G in some embodiments, or even higher values in some embodiments.

According to some embodiments, a health-monitor patch may include one or more sensors in addition to motion sensor 352 and accelerometer 330. For example, a health-monitor patch may include at least one physiological sensor 354 (e.g., cardiac sensor, temperature sensor, blood glucose sensor, blood oxygenation sensor, etc.) configured to sense at least one physiological parameter of a subject. A physiological sensor may comprise one or more electrodes configured to provide electrical connection to the skin of a subject in some embodiments. Other components that may be used in a physiological sensor include, but are not limited to, pressure transducers, acoustic transducers, temperature sensing elements (e.g., thermistors, infrared sensors), light sources (e.g., LEDs or laser diodes), and photodetectors.) One illustrative example of a physiological sensor comprises the AD8232 ECG chip available from Analog Devices, Inc.

of Norwood, Mass. Such a chip may be combined with electrodes arranged to contact the skin of a subject.

A physiological sensor 354 may include various signal-processing electronics and associated circuitry. For example, a physiological sensor 354 may comprise input amplifiers and noise filters that process received signals from monitoring electrodes or other detectors. Input amplifiers may include low-noise amplifiers and differential amplifiers. A physiological sensor 354 may be disposed, at least in part, in a same package with a health-monitor patch in some implementations, or may be formed as a separate monitor to be attached to the subject at a separate location and wirelessly, or via a wired link, transmit data to the health-monitor patch according to a predetermined communication protocol. In some implementations, a portion (e.g., a signal processing portion) of a physiological sensor may be incorporated on a printed circuit board assembly of a health-monitor patch, whereas electrodes or detectors for the sensor may be located off the PCB assembly. In some cases, a central processor of a health-monitor patch may comprise a portion of a physiological sensor and process signals from electrodes or other detectors to determine one or more physiological parameters. Examples of physiological parameters that may be sensed by one or more physiological sensors 354 include, but are not limited to, cardiac waveform, heart rate, heart-rate variability, arrhythmia, skin temperature, core temperature, respiration rate, plethysmography waveform, EKG waveform, blood oxygenation level, blood glucose level, hydration, blood pressure, etc.

In some embodiments, a health-monitor patch may include memory 320 that is external to and accessible to the processor 310. The memory 320 may be any one of or combination of the following types of memory: RAM, SRAM, DRAM, ROM, flash memory. The memory 320 may, for example, be used to store and/or buffer raw data from accelerometer 330 and/or physiological sensor 354, machine-readable instructions for processor 310, program data used by the processor for processing accelerometer data and/or physiological data, and/or activity data representative of an activity. In some embodiments, the memory 320 may additionally or alternatively be used to store diagnostic information about the health of the health-monitor patch, e.g., battery life, error status, etc., and/or technical information about the device, e.g., memory size, gravitational sensitivity, weight, battery model, processor speed, version of operating software, user interface requirements, etc. In some embodiments, the memory may also be used to store information pertinent to a user, e.g., user weight, height, gender, age, training goals, specific workout plans, activity-specific data for a user that may be used to identify an activity performed by the user or process data representative of an identified activity. According to some embodiments, the memory 320 may store tables of metabolic equivalents (METs), calibration values, and health guideline data that is used to determine health benefit levels for various activities.

In some embodiments, the memory 320 may additionally or alternatively be used to store data structures and/or code received from an external device, e.g., via a wired or wireless link. The data structures and/or code may, for example, be used to update one or more data processing applications used by the health-monitor patch. For example, one type of data structure may be data representative of an activity data pattern that may be used to identify a specific type of activity not previously recognized by the health-monitor patch, e.g., a new activity or an activity that is specific to an individual user of the health-monitor patch. As another example, a data structure may comprise a membership function, described below, defined for a new activity or redefined for an identifiable activity. According to some embodiments, the data structure may, for example, include one or more sample accelerometer traces and physiological data obtained during performance of the activity and/or may comprise identification data (e.g., membership functions) resulting from the processing of the accelerometer traces that may be used in an algorithm executed by the health-monitor patch to identify the activity. Further, in some embodiments, the memory 320 may be used to store updates and/or replacements to algorithms executed by the health-monitor patch. The stored data structures and algorithms may, for example, be used to reprogram and/or expand the functionality of the health-monitor patch to identify new activities or activities not previously recognized by the health-monitor patch and/or improve the accuracy or confidence of results calculated for identified activities.

In some embodiments, the memory 320 may also be used to store calibration and/or conversion data that is used by the processor 310 to characterize detected activities. Calibration data may, for example, be used to improve the accuracy of detected activity parameters (e.g., stride length, speed), and/or improve the accuracy of fitness metrics computed from detected activities. Conversion data may, for example, be used to convert a detected activity into an amount of expended human energy, e.g., calories burned, metabolic equivalents, etc.

According to some embodiments, a health-monitor patch may include a transceiver 340 and/or one or more data communication ports (e.g., a USB port, an RF communication port, a Bluetooth port) for communicating data between the health-monitor patch and one or more external devices such as a computer, tablet, cell phone, portable communication device, data processor, a sensor, another intelligent sensor, or a versatile sensor, any of which may be configured to communicate with other similar devices in a network such as the world-wide web or a local area network. A health-monitor patch may, for example, be configured to communicate via the transceiver 340 through a wired or wireless port to any device or combination or devices selected from the following list: a personal computer, laptop computer, tablet computer, PDA, a watch, an MP3 player, an iPod, a mobile phone, a medical device such as a blood glucose meter, blood pressure monitor, or InR meter, an electronic interactive gaming apparatus, intelligent training equipment, and an automobile system. Data retrieved from the memory 320 or to be stored in memory may, for example, be communicated between the health-monitor patch and an external device via the transceiver 340. In some embodiments, data transmitted from the health-monitor patch may be configured for routing to a data service device adapted to process data received from a health-monitor patch.

In some embodiments, power for the internal electronics of a health-monitor patch may be provided by at least one battery 305 and managed by a wake-up and power-management circuit 350. The battery may be small, e.g., a button-cell type, and may, for example, comprise one or more lithium-type batteries that may be rechargeable or replaceable. As just one example, a single lithium coin or button-cell, 3-volt battery having a capacity of about 230 mAh may be used (model CR2032 available from Renata SA of Itingen, Switzerland). Another embodiment of a health-monitor patch may include one or more model CR1616 batteries, though any suitable type of battery may alternatively be used in various embodiments. In some embodiments, a health-monitor patch may include power-generation or energy-harvesting hardware (e.g., a piezo-electric material or electric generator configured to convert mechanical motion into electric current, a solar cell, an RF or thermal converter). Power that is generated on board may be stored in a battery or charge-storage component such as a super capacitor. In some implementations, generated electrical current may be provided to a storage component via a diode bridge. One example of a suitable energy harvesting device is a microenergy cell MEC225 available from Infinite Power Solutions, Inc. of Littleton, Colo. In some embodiments, power generation components may be used in combination with a rechargeable battery as a source of power for a health-monitor patch. A voltage regulator chip (e.g., TPS78001 available from Texas Instruments of Dallas, Tex.) may be used to condition power from at least one power source before delivering the power to components of a health-monitor patch, according to some embodiments.

According to some embodiments, a battery 305 of a health-monitor patch may be recharged wirelessly. For example, a health-monitor patch may include a conductive coil that can inductively couple electromagnetic energy from an alternating magnetic field. Current from the coil may be provided to a rectifying circuit that converts the alternating current into a direct current that can be used to charge a battery 305.

In some implementations, wake-up and power-management circuitry 350 may include a motion sensor 352 that, in combination with the wake-up and power-management circuitry 350, identifies when a health-monitor patch is being moved in a manner that may be representative of an activity to be monitored. The wake-up and power-management circuitry 350 may, for example, comprise logic and control circuitry to enable, disable, reduce and/or increase power to various circuit elements shown in FIG. 3. Logic and control circuitry for the wake-up and power-management circuitry may, for example, comprise machine-readable instructions and utilized hardware of the processor 310, or may comprise machine-readable instructions and utilized hardware of an application specific integrated circuit.

In some embodiments, the motion sensor 352 may comprise one or more force sensitive switches, e.g., a piezo element configured to generate an electric signal representative of an amount of acceleration that a health-monitor patch experiences. In other embodiments, the motion sensor 352 may additionally or alternatively comprise one or more contact switches that close a circuit, or open a circuit, when the health-monitor patch is subjected to an acceleration, e.g., a "ball-in-tube" switch. Wake-up may, for example, be initiated when a frequency of switch closures exceeds a pre-selected value. In other embodiments, the sensor 352 may additionally or alternatively comprise one or more force-sensitive contact switches that close only when a health-monitor patch undergoes acceleration in excess of a pre-selected value.

Figure 8:
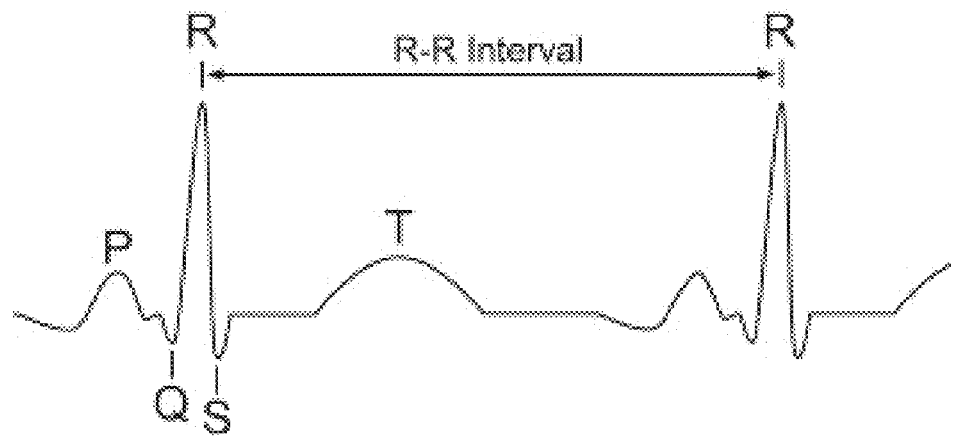
FIG. 8 illustrates a cardiac waveform.

According to some embodiments, a health-monitor patch may include an electro-optic display (e.g., a liquid-crystal display, an OLED display, one or more LEDs) and be configured to recognize one or more tapping sequences and/or motion gestures (e.g., moving the device in a figure-8 pattern, a circle pattern, a back-and-forth linear pattern). Responsive to recognition of a tapping sequence or gesture, a health-monitor patch may activate the display to communicate information or a summary of information stored on the patch. A tapping sequence or gesture may correspond to a particular information query, to which the health-monitor patch may respond by indicating with the display relevant information. According to one embodiment, the health-monitor patch may be tapped in a particular manner, and in response activate a number of LEDs to indicate that a user has reached an approximate percentage of an activity goal (e.g., illuminating 8 of 10 LEDs to signal approximately 80%). An activity goal may be preprogrammed into the health-monitor patch by a user of physician using another electronic device such as a computer or smart phone that can communicate wirelessly with the health-monitor patch. Information about progress toward one or more activity goals can be communicated by the device (e.g., walked 30% of a goal of 3 miles, ran 60% of a goal of 8 miles, swam 90% of a goal of 60 laps, achieved 70% of creditable health-beneficial activity for the day, achieved 50% of a recommended number of health credits for a week, etc.) A display may also be used to communicate other information responsive to particular tapping sequences or gestures, e.g., battery life, pace comparison (ahead of, or behind, best pace for an activity), heart rate, calories burned, etc.

Data may also be communicated to and from a health-monitor patch using a wireless communication protocol (e.g., Bluetooth, BluetoothLE, Bluetooth Smart, a modified Bluetooth protocol, Wi-Fi, etc.). For example, a wireless transceiver and antenna may be included with a health-monitor patch and used to transmit and receive data to and from a remote device such as a smart phone, smart watch, computer, tablet, etc.

According to some embodiments, a health-monitor patch may include at least one light source 286 and at least one photodetector 287. The at least one light source and photodetector may be used, for example, for sensing one or more physiological parameters of a subject, e.g., blood oxygenation level, plethysmography waveforms, blood glucose level, blood flow rate, etc. In some embodiments, the light source 286 may comprise a high-brightness infrared (IR) photodiode and a shorter wavelength photodiode. In recent years, progress in indium-gallium-nitride LED technology has yielded devices with both lowered junction voltage and increased radiated intensity. Using InGaN technology, and applying power management techniques described in U.S. patent application Ser. No. 13/840,098, to which this application claims priority, may provide a health-monitor patch capable of measuring heart rate and/or other physiological parameters that can run for a week or more on one or more coin-cell silver-oxide batteries. The photodetector 287 may be any suitable photodetector (e.g., one or more silicon photodiodes that may include a wavelength filter), and may be mounted to detect light from the light source that is scattered or reflected from the subject.

Figure 4:
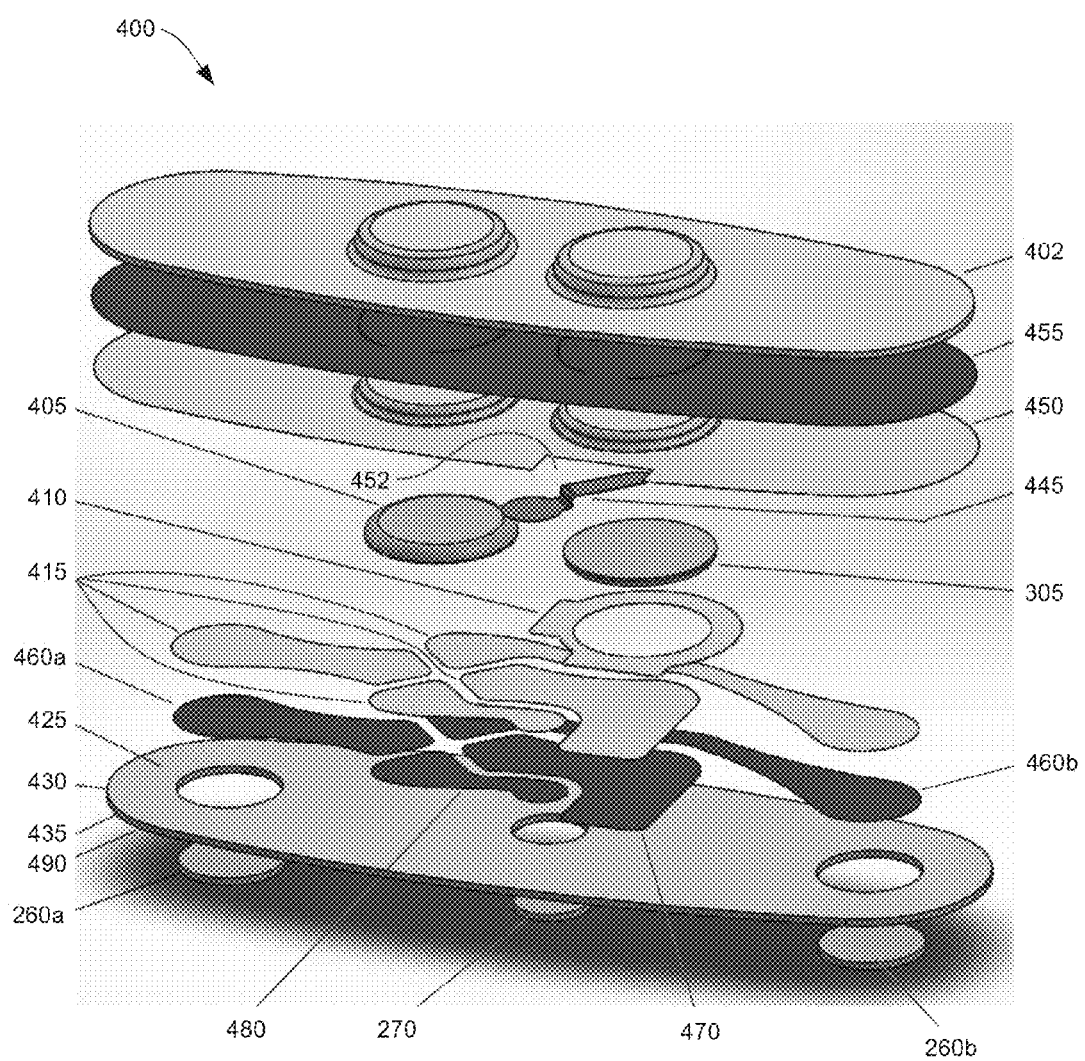
FIG. 4 depicts an exploded view of a disposable health-monitor patch, according to some embodiments.

FIG. 4 depicts an exploded view of a disposable health-monitor patch 400, according to some embodiments. A flexible strip assembly of a disposable health-monitor patch may include a first PCB assembly 405, a battery 305, and a plurality of flexible materials. At least some of the flexible materials or layers may comprise a sheet formed from solid material (e.g., a plymer film, cloth, polymer or cloth mesh, etc.) that provides tensile strength and shape retention for a health-monitor patch. For example, one or more layers may comprise flexible adhesive tape or films. Some layers may be deposited as a liquid or gel, according to some embodiments. In some cases, the PCB assembly may comprise a flexible PCB.

According to some embodiments, a battery strap 445 may provide a connection between a first terminal of the battery 305 (e.g., the positive terminal) and a battery conductor 480. The battery strap and conductor may be formed from a conductive metal and/or conductive polymer (e.g., a conductive carbon vinyl film which may or may not be coated with a film comprising silver. The battery 305 may be a coin-cell type battery having a diameter between about 10 mm and about 20 mm, and may be located adjacent to an insulating ring 410 that helps to electrically isolate the two terminals of the battery. A second terminal of the battery may electrically connect to a noise/ground conductor 470. The noise/ground conductor may also connect to a noise electrode 270 on the disposable health-monitor patch 400. According to some implementations, the noise/ground conductor 470 may further connect to a ground contact (not shown) located on the PCB assembly 405.

There may be additional conductors that connect to the monitor electrodes of a disposable health-monitor patch. For example a first monitor conductor 460a may provide electrical connection between a first monitor electrode 260a and a first signal input pad (not shown) of the PCB assembly 405. A second monitor conductor 460b may provide electrical connection between a second monitor electrode 260b and a second signal input pad (not shown) on the PCB assembly 405. The first monitor conductor 460a, the second monitor conductor 460b, the battery conductor 480, and the noise/ground conductor 470 may be formed from a conductive polymer which may or may not be adhesive. In some embodiments these conductors may be formed from a carbon vinyl polymer or coated vinyl polymer. An example of a coated vinyl polymer that may be used for a flexible conductor is model 6355, available from Coveris Advanced Coatings of Matthews, N.C. In some implementations, one or more of the conductors may be formed from a flexible PCB. In some embodiments, the first monitor conductor 460a, the second monitor conductor 460b, the battery conductor 480, and the noise/ground conductor 470 may be cut or punched from a film of the conductive polymer.

Below the conductors may be a conductor adhesion layer 425 to which the conductors may be adhered. The conductor adhesion layer 425 may retain the conductors in place as the disposable health-monitor patch flexes on a subject. In some embodiments, the conductor adhesion layer 425 may be a silicone adhesive layer that is electrically insulating. According to some implementations, the conductor adhesion layer 425 may have adhesive surfaces on opposing sides (e.g., double-sided adhesive). An example of a conductor adhesion layer 425 is model 96022 silicone adhesive, available from 3M Corporation of St. Paul, Minn. According to some embodiments, the conductor adhesion layer 425 may be cut and/or punched from a film of the adhesive material.

According to some embodiments, there may be conductive adhesive elements 415 located above the battery and signal conductors. The conductive adhesive elements may have adhesion surfaces on opposing sides. These elements may be formed in a similar shape to the conductors 460a, 460b, 470, 480 from a flexible conductive adhesive film. The conductive adhesive elements 415 can provide electrical connection between the underlying conductors and contact pads on the PCB assembly and terminals on the battery 305. The conductive adhesive elements 415 can also adhere the underlying conductors, PCB assembly, and battery together into a flexible assembly. A conductive adhesive element may be formed from adhesive film, model 9719, available from 3M Corporation of St. Paul, Minn., according to some embodiments. The conductive adhesive elements 415 may be cut or punched from a film of conducting adhesive.

In some cases, an insulating layer 430 may be located below the conductor adhesion layer 425. The insulating layer 430 may provide some stiffness to the lower layers and help retain the monitor electrodes 260a, 260b and the noise electrode 270. In some cases, insulating layer 430 may comprise a foam material having an adhesive surface on one side, an example of which is model 1774W, available from 3M Corporation of St. Paul, Minn. The adhesive surface may be facing the conductors 460a, 460b, 470, 480, for example. The insulating layer 430 may be cut or punched from a film of the material.

In some embodiments, there may be a surface adhesion layer 435 that adheres to the insulating layer 430. An example of a surface adhesion layer 430 is model 96022 silicone adhesive, available from 3M Corporation of St. Paul, Minn., though other suitable adhesion layers may be used. According to some embodiments, the surface adhesion layer 430 may be cut and/or punched from a film of the adhesive material.

According to some aspects, a skin adhesion layer 490 may be attached to the insulator layer 430. The skin adhesion layer 490 may include an adhesion surface 252 that provides a durable adhesion to the skin of the subject. Any suitable skin adhesive material may be used for the skin adhesion layer 490. According to some embodiments, a suitable acrylic skin adhesive available from Avery Dennison of Glendale, Calif. may be used as a skin adhesion layer 490. One example of a skin adhesion layer 490 is a Tegaderm adhesive, model 1626W, available from 3M Corporation of St. Paul, Minn., though other biocompatible adhesion layers may be used. In some implementations, a hydrocolloid adhesive, model H011, available from Adhesive R&D of Eau Claire, Wis. may be used for the skin adhesion layer. A skin adhesion layer 490 may include a release liner (not shown) over the adhesion surface, that is removed prior to adhering the disposable health-monitor patch 400 to a subject. An example release liner is model 1361 liner, available from 3M Corporation of St. Paul, Minn. In some implementations, a skin adhesion layer 490 may be cut and/or punched from a film of the material.

Upper layers of a disposable health-monitor patch 400 may include an insulating adhesive layer 450 and an electrostatic discharge (ESD) shield 455 that extend over the battery 305, the PCB assembly 405, and a majority of the conductive adhesive elements 415. In some cases, there may be a hole or notch in the insulating adhesive layer 450 that allows the noise/ground conductor 470 to electrically connect to the ESD shield 455, which may be located adjacent to the insulating adhesive layer 450. The insulating adhesive layer 450 may have adhesive surfaces on opposing sides, or may have a single adhesive surface. An example insulating adhesive layer is adhesive model 9474LE, available from 3M Corporation of St. Paul, Minn., though other insulating adhesive layers may be used in other embodiments. An example double-sided, insulating, adhesive layer having different adhesion properties on opposing sides (e.g., a differential adhesive) include adhesive model 9425, available from 3M Corporation of St. Paul, Minn. The insulating adhesive layer 450 may be cut and/or punched from a film of the adhesive material.

In some embodiments, an ESD shield 455 may extend over at least a portion of the first monitor conductor 460a and at least a portion of the second monitor conductor 460b. The ESD shield may further electrically connect to the noise electrode 270 via the noise/ground conductor 470. The ESD shield may be insulated from the first monitor conductor and the second monitor conductor, but be located in close proximity (e.g., less than about 2 mm) to the two conductors (e.g., arranged as parallel plates in some locations). The ESD shield may be formed from a conductive polymer, according to some embodiments. An example conductive polymer is coated carbon vinyl film, model 6355, available from Coveris Advanced Coatings of Matthews, N.C., though uncoated conductive films may be used.

According to some embodiments electrical noise transmitted across the skin of the subject may be picked up by the noise electrode 270 and conducted to the ESD shield 455. This noise may then couple into the first monitor conductor 460a and the second monitor conductor 460b from the ESD shield due to the close proximity of the ESD overlying the first monitor conductor 460a and second monitor conductor 460b. In some embodiments, the amount of signal coupled to each monitor electrode may have similar amplitudes (e.g., within about ±15%). A differential amplifier may be arranged at a signal input of the PCB assembly 405 to amplify signals received from the first monitor electrode 260a and second monitor electrode 260b. Since the noise is coupled into the two conductors and inputs of the differential amplifier, it may be reduced or cancelled via common-mode rejection.

According to some embodiments, there may be an adhesive cover layer 402 attached over the ESD shield 455 that covers the disposable health-monitor patch 400. The adhesive cover layer 402 may comprise cloth, foam, a flexible polymer (such as silicone), or any other suitably flexible material. In some embodiments, a cover layer 402 may comprise a second layer of the same material used for the insulating layer 430. The cover layer may be cut or punched from a film of the material. In some instances, the cover layer 402 and insulating layer 430 may comprise sealed foam or a suitable water resistant or waterproof material to reduce ingress of water to the PCB assembly 405 and battery 305.

Figure 5:
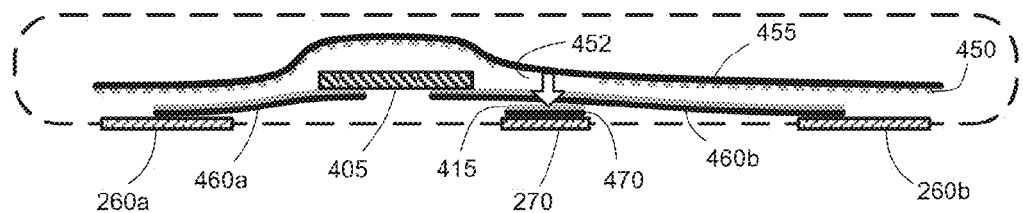
FIG. 5 illustrates a noise suppression configuration and conductive adhesive in a circuit of a health-monitor patch, according to some embodiments.

Some components of a disposable health-monitor patch are depicted in the elevation view of FIG. 5, according to some embodiments. The depiction shows a PCB assembly 405 that connects to the first monitor electrode 260a via a conductive adhesive element (depicted as a gray line) and the first monitor conductor 460a. The PCB assembly 405 also electrically connects to the second monitor electrode 260b via a conductive adhesive element (gray line) and the second monitor conductor 460b. The battery 305 and its conductors are not depicted in FIG. 5 to simplify the drawing.

In some implementations, the ESD shield 455 is disposed over the PCB assembly 405, the first monitor conductor 460a, and the second monitor conductor 460b. There may be an insulating adhesion layer 450 between the ESD shield 455 and the conductive adhesive elements. The insulating layer may include an opening 452 (also depicted in FIG. 4) between the ESD shield 455 and the conductive adhesive element 415 that is located over the noise/ground conductor 470. The opening allows an electrical connection to be made between the ESD shield 455 and the noise electrode 270 when the layers of the health-monitor patch are all pressed together.

Figure 6:
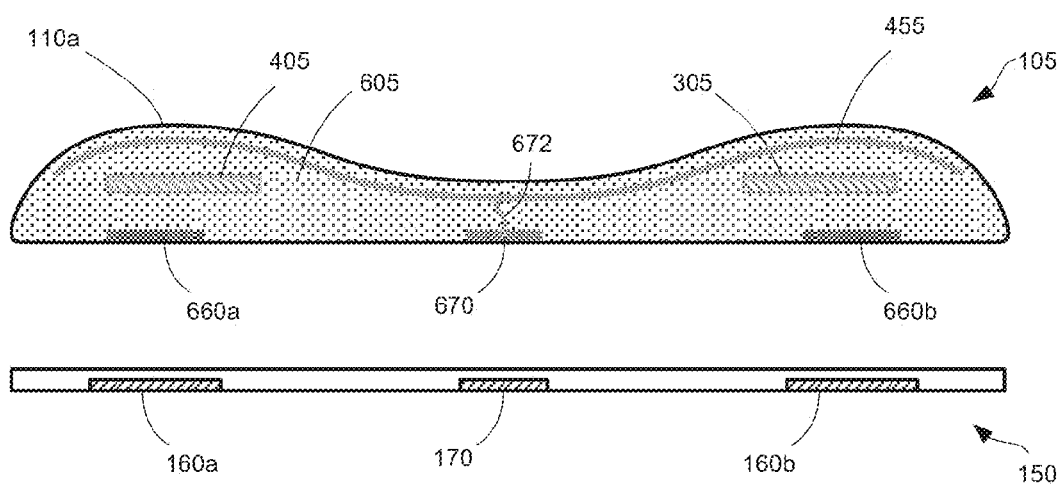
FIG. 6 illustrates infused conductors in a flexible strip assembly, according to some embodiments.

Further details of a repeated-use health-monitor patch 100 are depicted in the elevation view of FIG. 6, for some implementations. The illustration shows an arrangement of components for the device illustrated in FIGS. 1A-1C, according to some embodiments. Within the flexible strip assembly 105, there may be a PCB assembly 405 and a battery 305. The flexible strip assembly 105 may further include conductive elements (not all shown) that provide electrical connection between terminals of the battery and power/ground pads on the PCB assembly and one or more noise electrodes or sensing components, and between signal inputs on the PCB assembly and monitor electrodes 160a, 160b. The noise electrode and monitor electrodes may be located on the replaceable electrode strip 150, which is shown separated from the flexible strip assembly.

According to some embodiments, there may be electrical connections between various components of a health-monitor patch. For example, a patterned flexible PCB may be used to form electrical connections between a monitor electrode and a PCB assembly 405. The inventors have recognized and appreciated that linkages between a flexible conductor (e.g., a flexible PCB) and a more rigid electrical component (e.g., a PCB assembly 405) can be improved by adding strain-relief material at an interface of the flexible conductor. For example, silicone, polyimide, or a thermal set adhesive may be added to reinforce and provide strain relief at a junction between a flexible conductor and a more rigid electrical component.

In some embodiments, the flexible strip assembly 105 may be formed in part from flexible silicone. For example, the silicone may be applied in gel or liquid form into a mold to cover electronic components of a health-monitor patch. The resulting silicone casing 605 may extend entirely around the battery 305, the PCB assembly 405, and the associated conductors. The silicone may then be cured, so that the assembly 105 can be highly flexible and completely waterproof. A waterproof enclosure may allow the health-monitor patch to be worn on a subject and immersed in water. Further, adhesives used for the replaceable electrode strip 150 form watertight seals with the silicone casing 605 and skin of a subject. The inventors have recognized and appreciated that conventional activity monitors that sense heart rate do not perform well or at all when immersed in water. The silicone enclosure may allow the health-monitor patch to monitor activity and physiological parameters of a swimmer, surfer, windsurfer, kiteboarder, etc.

Since, in some implementations, the on-board battery may be fully encased in silicone, wireless charging may be used to recharge the on-board battery. In some embodiments, a coil and rectifying circuit may be included in a health-monitor patch so that electromagnetic energy may be wirelessly coupled to the coil from a wireless charger. Energy coupled to the coil may be rectified and used to charge the battery.

Although silicone provides a flexible and robust environmental seal, it is an electrical insulator. The inventors have conceived of locally modifying the silicone so that electrical connection through the silicone to the monitor and noise electrodes of the replaceable electrode strip 150 can be achieved. According to some embodiments, the electrical connections do not require metal wires or inflexible metal pads at the surface of the silicone casing 605.

According to some embodiments, the silicone casing may be infused with carbon or other conductive materials at surface locations that correspond to locations of the monitor electrodes 160a, 160b and noise electrode(s) 170 on the replaceable electrode strip 150. For example, the flexible strip assembly 105 may include a first infused monitor electrode 660a and a second infused monitor electrode 660b. The flexible strip assembly may further include one or more infused noise electrodes 670.

The carbon-infused electrodes may be formed, according to some embodiments, using a double-injection process. For example, a first injection of uncured, carbon-infused silicone may be used to form the infused electrodes 660a, 660b, 670 at the correct locations. Conductive carbon powder may be premixed into the silicon to make the silicone conductive. A second silicone injection may then be used to form the remaining casing 605 of the flexible strip assembly. The second silicone injection may comprise insulating silicone.

The first injection may be uncured, partially cured, or fully cured prior to the second injection.

Internal conductors 672 (e.g., conductors on a flexible PCB or conductors made from a flexible conductive film) may electrically connect to a corresponding infused electrode. (Not all conductors are shown in FIG. 6.) For example, the carbon-infused silicone may be injected around an exposed end of a conductor. The conductor may then provide an electrical connection to a signal input on the PCB assembly 405 or to the ESD shield 455. The infused electrode may provide electrical conduction between a conductor and another conductive element on the replaceable electrode strip.

Figure 7A:
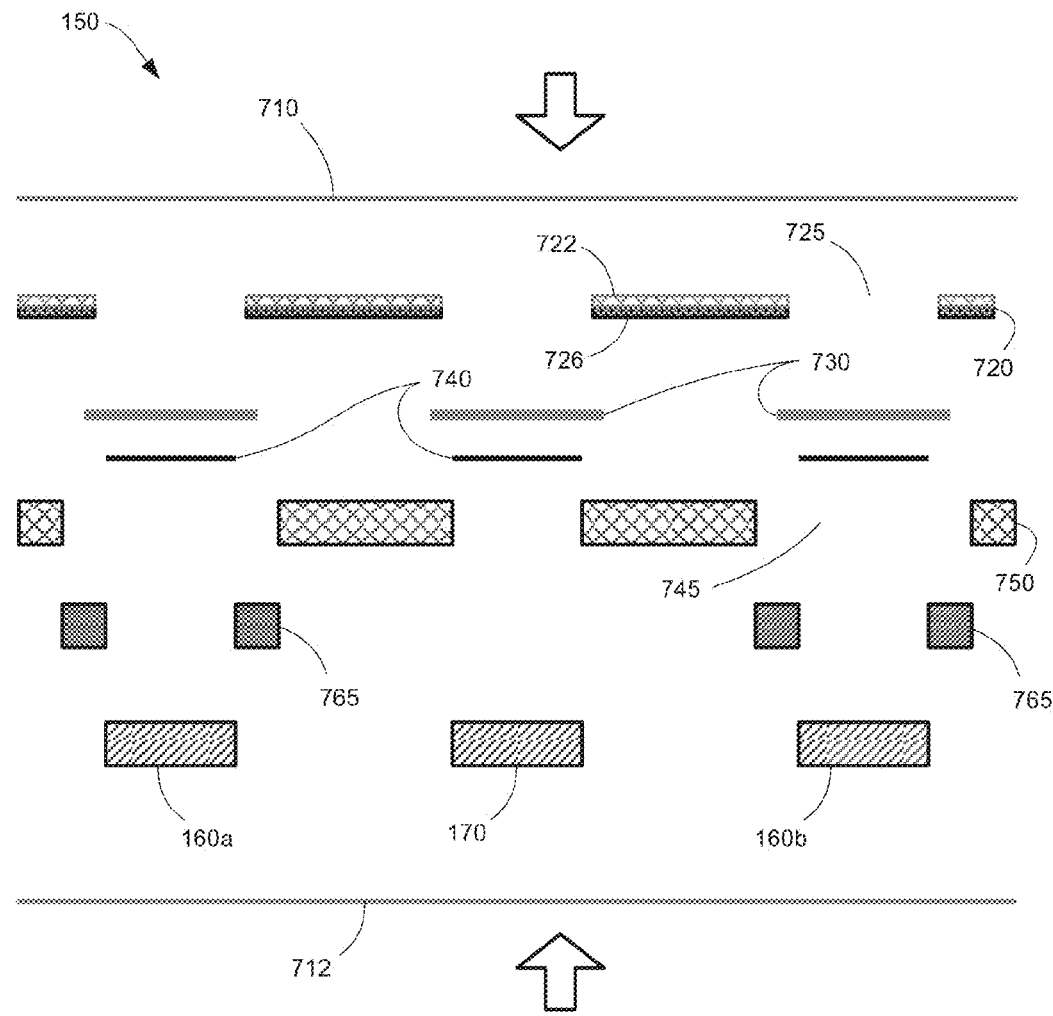
FIG. 7A depicts an exploded view of components for a replaceable electrode strip, according to some embodiments.

An embodiment showing further details of a replaceable electrode strip 150 is illustrated in FIG. 7A. The components are shown in an exploded elevation view in FIG. 7A and depicted in an assembled elevation view in FIG. 7B. In some implementations, a replaceable electrode strip may comprise a first release liner 710 sealing a top adhesive surface of the replaceable electrode strip and a second release liner 712 covering a skin adhesion surface 152 of the replaceable electrode strip. In some implementations, the first and second release liners may be release liner model 1361, available from 3M Corporation of St. Paul, Minn., though other liners may be used in other embodiments. The first release liner may be removed prior to adhering the replaceable electrode strip 150 to the bottom (skin-side) surface of the flexible strip assembly 105. The second release liner may be removed prior to adhering the flexible strip assembly and replaceable electrode strip to the skin of a subject.

A replaceable electrode strip 150 may further include a patch adhesion layer 720 that provides adhesion of the replaceable electrode strip to the flexible strip assembly 105 (e.g., to the silicone casing 605). The patch adhesion layer may comprise adhesive surfaces 722, 726 on opposing sides in some cases. In some implementations, the adhesive surfaces may be formed of a same material. In other embodiments, the adhesive surfaces may be formed of a different material. Examples of double-sided adhesives formed of same materials may include adhesive models 96042 or 9474LE, available from 3M Corporation of St. Paul, Minn. An example double-sided adhesive having different adhesion properties on opposing sides (e.g., a differential adhesive) include adhesive model 9425, available from 3M Corporation of St. Paul, Minn. The patch adhesion layer may be configured to adhere to silicone on a first adhesive side 722 and an underlying layer of the replaceable electrode strip on a second adhesive side 726.

In some embodiments, the patch adhesion layer 720 may include vias 725 that expose conductive adhesive disks 730 when the first release liner 710 is removed. The vias 725 may have a diameter between about 5 mm and about 20 mm, according to some embodiments. The conductive adhesive disks 730 may have a diameter approximately 2 mm to approximately 6 mm larger than the diameter of the vias 725.

In some implementations, the conductive adhesive disks 730 may be formed from conductive adhesive model 9713, available from 3M Corporation of St. Paul, Minn., though other conductive adhesives may be used in some cases. The conductive adhesive disks 730 may adhere to infused silicone electrodes 660a, 660b, 670 on one side and to conductive disks 740 on an opposing side and provide electrical connections between the infused electrodes and conductive disks. The conductive adhesive disks 730 may also adhere to the patch adhesion layer 720 and retain the conductive disks 740 in a desired location (e.g., aligned to electrodes 160a, 160b, 170). The flexible conductive disks 740 may be formed from a conductive polymer, such as a carbon vinyl film model 6355, available from Coveris Advanced Coatings of Matthews, N.C., though other conductive films may be used in some cases. A diameter of the conductive disks 740 may be between approximately 1 mm and approximately 6 mm smaller than the diameter of the conductive adhesive disks 730, according to some embodiments. In some embodiments, a diameter of the conductive disks 740 may be equal to or larger than the diameter of the conductive adhesive disks 730.

A replaceable electrode strip 150 may further include a skin adhesion layer 750. The skin adhesion layer 750 may be electrically insulating and include vias 745 that expose the conductive disks 740 to underlying electrodes 160a, 160b, 170. The diameter of the vias 745 may be less than or greater than the diameter of the conductive disks 740. An example of a skin adhesion layer 750 is a Tegaderm adhesive, model 1626W, available from 3M Corporation of St. Paul, Minn., though other biocompatible adhesive layers may be used. In some implementations, a hydrocolloid adhesive, model H011, available from Adhesive R&D of Eau Claire, Wis. may be used for the skin adhesion layer 750.

The vias 745 of the skin adhesion layer 750 may accommodate the monitor electrodes 160a, 160b and the noise electrode(s) 170, according to some embodiments. These electrodes may be formed from a hydrogel, e.g., X863 Hydrogel available from Adhesive R&D of Eau Claire, Wis., though any other suitable hydrogel may be used. The diameter of the electrodes may be between approximately 5 mm and approximately 20 mm, in some cases. In some embodiments, the diameter of the electrodes may be between approximately 8 mm and approximately 16 mm.

In some implementations, one or more of the electrodes 160a, 160b, 170 may be surrounded laterally by an adhesive ring 765. The adhesive ring may be insulating, according to some embodiments. The adhesive rings may be formed from adhesive model 1774W, available from 3M Corporation of St. Paul, Minn., though other adhesives may be used to form adhesive rings 765.

Figure 7B:
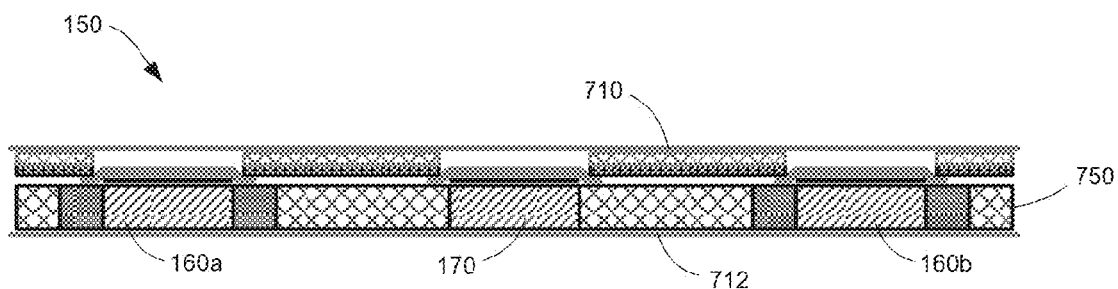
FIG. 7B depicts a cross section of a replaceable electrode strip, according to some embodiments.

FIG. 7B shows components of a replaceable electrode assembly 150 pressed together to bond the different layers and components into an assembly. In some embodiments, the hydrogel may be injected after pressing the layers and other components together and prior to applying the second release liner 712. According to some embodiments, the flexible layers and components of the replaceable electrode assembly 150 (apart from the hydrogel electrodes) may be cut and/or punched to a suitable shape when manufacturing the assembly. Referring again to FIG. 4, flexible layers and components of a disposable health-monitor patch 400 (apart from the hydrogel electrodes, PCB assembly, and battery) may be cut and/or punched to a suitable shape when manufacturing the assembly. The inventors have recognized and appreciated that multiple layers and components of a replaceable electrode assembly 150 and a disposable health-monitor patch 400 may be formed and assembled using reel-to-reel or "converter" manufacturing processes. This can greatly reduce manufacturing costs for producing a health-monitor patch or replaceable electrode strip.

In some embodiments, two or more "levels" of a disposable health-monitor patch or replaceable electrode strip may be assembled using a converter process to form a first composite. Separately, two or more additional levels may be assembled using a converter process to form a second composite. Then, the two composites may be assemble using a converter process.

For example and referring to FIG. 7A, a first composite may be assembled in a converter process by unrolling a release liner 710 from a first roll (level 1), punching vias 725 in a sheet from a second roll comprising patch adhesion layer 720 (level 2), and perforating conductive adhesive disks 730 from a third roll comprising a conductive adhesive (level 3). Perforating a layer may allow the disks 730 (or other component) to be weakly retained in the sheet of material, and subsequently broken or torn free from the sheet when bonding to another layer.

The three levels may then be pressed together to form a first composite, and excess material from the conductive adhesive roll may be removed. Similar processing may be used to assemble the conductive disks 740 (level 4), skin adhesion layer 750 (level 5), and adhesive rings 765 (level 6) to form a second composite. The first and second composites may then be aligned and pressed together in a converter process. Subsequently, the hydrogel electrodes 160a, 160b, 170 may be injected and the second release liner 712 applied. Finally, the replaceable electrode assembly 150 may be punched from the assembled composites and packaged. Other suitable manufacturing processes may be used in other embodiments.

When placed in operation, a health-monitor patch (repeated-use or disposable) may detect full PQRST waveform profiles or portions of PQRST waveform profiles of a subject continuously or intermittently, according to some implementations. An illustration of a PQRST waveform profile is depicted in FIG. 8. The detected waveforms may be processed (e.g., by processor 310, digital signal processing circuitry, or any suitable signal processing circuitry) to determine one or more physiological parameters. Physiological parameters that may be determined by a health-monitor patch from cardiac waveforms may include heart rate, inter-beat interval (IBI), heart rate variability (HRV), arrhythmia, and respiration rate, for example.

Figure 9:
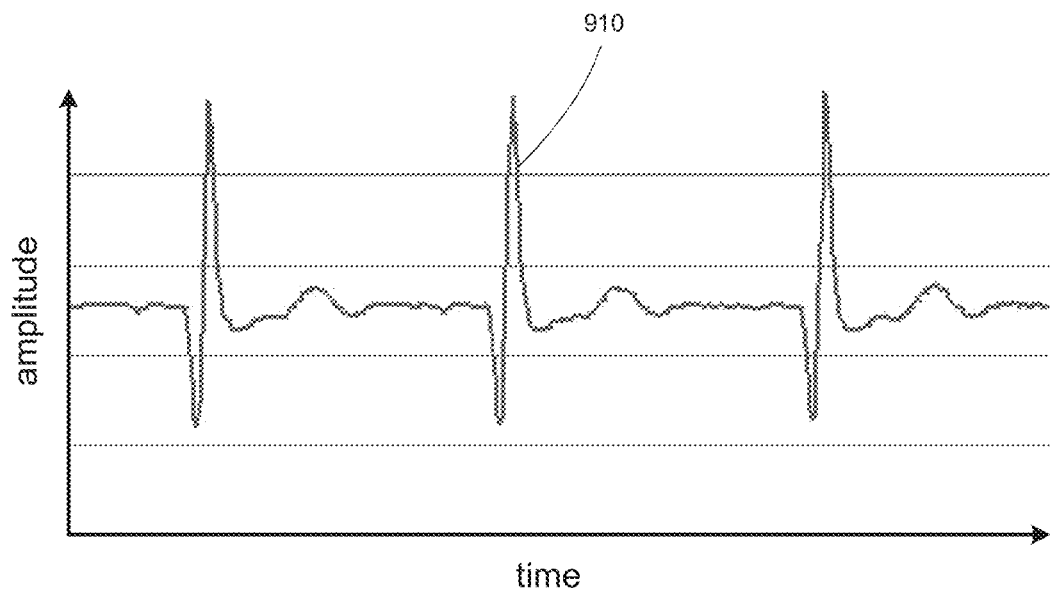
FIG. 9 illustrates a cardiac waveform obtained with a health-monitor patch.

According to some embodiments, electronic filtering may be used to pre-process a cardiac waveform. For example, filtering may be used to reduce noise, pass or block certain frequency components, or emphasize aspects of a PQRST waveform so that a particular parameter (e.g., heart rate, HRV, arrhythmia, etc.) may be determined by a processor 310 more accurately, for example. A cardiac waveform 910 recorded by a health-monitor patch of an example embodiment is plotted in FIG. 9. The signal has been pre-processed by on-board circuitry to emphasize aspects of the R wave, so that heart rate may be determined more accurately. According to some embodiments, different signal processing schemes may be employed to emphasize selected aspects of a cardiac waveform, so that a recorded or analyzed waveform may be different from those shown in FIG. 8 and FIG. 9.

According to some implementations, power conservation for a health-monitor patch may, at least in part, be based on cardiac data received from a cardiac sensor and/or motion data received from an accelerometer. Power conservation methods based on cardiac data may run in parallel with or in combination with power conservation methods based on motion data. In some cases, a power conservation mode of operation may be determined in part based upon a health condition of the subject. For example, recovering patients or individuals presenting a health impairment may need more continuous and/or full monitoring of cardiac waveform and/or activity/motion data, whereas less monitoring of cardiac waveforms and activity data may be needed for fit individuals. Selection or setting of power-conservation mode options may be made via wireless communication with the health-monitor patch or via a tapping sequence or gesture recognizable by the health-monitor patch.

To extend battery life, a health-monitor patch may cycle through one or more operational modes that consume different amounts of power depending on the state of the subject. As just one illustrative embodiment of power conservation, motion data may be analyzed by a system processor to determine that a subject is in an inactive state (e.g., sitting, lying, riding in a vehicle, etc.). A health-monitor patch may then determine that at least power to an accelerometer may be reduced. In some embodiments, circuitry and processing algorithms associated with the accelerometer may enter a sleep or reduced-power mode. In some embodiments, a cardiac sensor of the same health-monitor patch may also enter a sleep mode in which a full cardiac waveform is not recorded. Instead, portions of a cardiac waveform (e.g., only R-wave portions), or none of a cardiac waveform, may be recorded and/or processed. In some implementations, portions of the cardiac waveform may be recorded and processed intermittently (e.g., skipping one or more beats between recordings). In other embodiments, a cardiac sensor may continue to sense a full cardiac waveform while an inactive state of the subject has been detected (e.g., to monitor a cardiac parameter for a patient).

In some embodiments, a full-power continuous detection mode may be automatically activated when the health-monitor patch determines that the subject is active based on data from the accelerometer. In some implementations, a power management circuit of a health-monitor patch may place a cardiac sensor in a power-conserving state when a subject is active. For example, a health-monitor patch may determine that a subject's heart rate is stable during an activity, and may then place the cardiac sensor in a power-conserving state in which portions of the cardiac cycle are monitored continuously or intermittently.

Additional examples of power-conserving modes include, but are not limited to, a beat-detect mode, a QRS-detect mode, and a full-wave mode. In a beat-detect mode, a heart monitor may sleep for a period of time between each heartbeat of a subject and awake in time only to determine a point or timing in the cardiac waveform that is sufficient to indicate an inter-beat interval (IBI). For example, the cardiac sensor may awake in time to detect a portion of the cardiac waveform corresponding to an R wave. In some implementations, the cardiac signal may be fed to a comparator or processor configured to detect a threshold crossing or change in slope (e.g., location of a peak) of the R wave. A comparator may require less power to operate than circuitry needed to capture and analyze a portion of the cardiac waveform.

In a QRS-detect mode, a cardiac sensor may sleep for a period of time between each heartbeat of a subject and "awake" in time to capture a QRS waveform for subsequent analysis. The QRS waveform may, for example, be analyzed by a processor for arrhythmia, heart rate variability, and/or respiration rate, according to some implementations. In some embodiments, respiration rate may be determined from an envelope of the R-wave over multiple cardiac cycles.

In a full-wave mode of operation, a heart monitor may operate continuously to capture a full cardiac waveform for multiple beats. A full-wave mode of operation may be executed periodically to ascertain the timing of P or R waves, for example, and determine an interval of sleep for a cardiac monitor between heartbeats. In some implementations, a full-wave mode of operation may be executed when a subject becomes active, or may be executed when a subject's activity is found to be moderate and/or vigorous. In some implementations, a user may command continuous monitoring of a cardiac waveform and/or other physiological parameters irrespective of the user's activity by communicating wirelessly with, or tapping a sequence on, the health-monitor patch that can be detected by the motion sensor, processed, and recognized by the health-monitor patch's processor as a command to record full-wave, continuous data.

Additional embodiments of power-conserving modes and processing cardiac signals are described in U.S. Patent Application Pub. No. 2015-0119728, incorporated by reference above.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, and/or method described herein. In addition, any combination of two or more such features, systems, articles, materials, and/or methods, if such features, systems, articles, materials, and/or methods are not mutually inconsistent, is included within the inventive scope of the present disclosure.

The above-described embodiments of the invention can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single computer or distributed among multiple computers.

In this respect, various aspects of the invention, e.g., processing signals from monitor and noise electrodes, may be embodied at least in part as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various embodiments of the technology discussed above. The computer readable medium or media can be transportable, such that the program or programs stored thereon can be loaded onto one or more different computers or other processors to implement various aspects of the present technology as discussed above.

Various aspects of a health-monitor patch described above may be implemented in hardware, software, firmware, or a combination thereof. For example, any of the operational aspects of a health-monitor patch which involve processing data, handling data, and/or communications may be implemented as stored machine-readable instructions that are executable by a processor and embodied on at least one tangible, computer-readable storage device. The instructions may be executed or placed in operation on a digital processor of a health-monitor patch. In some implementations, instructions may be placed in operation on a central hub or server that operates in combination with operation of a health-monitor patch.

The terms "program" or "software" are used herein in a generic sense to refer to any type of computer code or set of machine-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single processor, but may be distributed in a modular fashion amongst a number of different processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, may be used to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed is:

1. A method for forming a component of a wearable monitor for a subject, comprising:
   using a first roll of material, forming a first component layer that incorporates a first circuit component;
   using a second roll of material, forming a second component layer that incorporates a second circuit component;
   adhering a flexible, conductive adhesive film to the first circuit component; and
   electrically connecting the first circuit component to the second circuit component via the flexible, conductive adhesive film disposed between the first and second component layers so as to establish a conductive path for carrying a signal indicative of a monitored characteristic of the subject between the first circuit component and the second circuit component of the wearable monitor via the flexible, conductive adhesive film.

2. The method of claim 1, wherein the first circuit component and the second circuit component are laterally displaced from each other.

3. The method of claim 1, further comprising forming the flexible, conductive adhesive film using a third roll of material.

4. The method of claim 1, wherein the first circuit component comprises a processor that is configured to process the signal to evaluate the monitored characteristic of the subject.

5. The method of claim 4, further comprising:
   incorporating the first and second component layers and the flexible, conductive adhesive film into the wearable monitor, wherein:
   the wearable monitor comprises a skin adhesion surface and a release liner releasably attached to the skin adhesion surface; and
   the second circuit component comprises a monitor electrode configured and arranged to be exposed at the skin adhesion surface when the release liner is removed from the skin adhesion surface.

6. A method for forming a component of a wearable monitor for a subject, comprising:
   providing a first component layer that incorporates a first circuit component;
   adhering a flexible, conductive adhesive film to the first circuit component so as to establish a conductive path for carrying a signal indicative of a monitored characteristic of the subject between the first circuit component and a second circuit component of the wearable monitor via the flexible, conductive adhesive film; and
   incorporating the first component layer and the flexible, conductive adhesive film into an electrode strip that is releasably attachable to another component of the wearable monitor that includes a processor configured to process the signal to evaluate the monitored characteristic of the subject, wherein:
   the electrode strip comprises first and second adhesion surfaces on opposing faces of the electrode strip and first and second release liners releasably attached to the first and second adhesion surfaces, respectively; and
   the first circuit component comprises an electrode that is exposed at the first adhesion surface when the first release liner is removed from the first adhesion surface.

7. The method of claim 6, wherein providing the first component layer comprises forming the first component layer using a first roll of material.

8. The method of claim 7, further comprising forming the flexible, conductive adhesive film using a second roll of material.

9. The method of claim 6, further comprising:
   providing a second component layer that incorporates the second circuit component; and
   electrically connecting the first circuit component to the second circuit component via the flexible, conductive adhesive film disposed between the first and second component layers so as to establish the conductive path.

10. The method of claim 9, wherein the second circuit component comprises a conductive disk that is exposed at the second adhesion surface when the second release liner is removed from the second adhesion surface.

11. The method of claim 9, wherein:
providing the first component layer comprises forming the first component layer using a first roll of material; and
providing the second component layer comprises forming the second component layer using a second roll of material.

12. The method of claim 11, further comprising forming the flexible, conductive adhesive film using a third roll of material.

* * * * *